United States Patent
Tohi et al.

(10) Patent No.: US 7,241,848 B2
(45) Date of Patent: Jul. 10, 2007

(54) PROCESS FOR PREPARING LOW MOLECULAR WEIGHT OLEFIN (CO)POLYMER AND POLYMERIZATION CATALYST USED THEREFOR

(75) Inventors: Yasushi Tohi, Sodegaura (JP); Naomi Urakawa, Sodegaura (JP); Koji Endo, Sodegaura (JP); Koji Kawai, Sodegaura (JP); Kazunori Okawa, deceased, late of Otake (JP); by Chiemi Okawa, legal representative, Otake (JP); Toshiyuki Tsutsui, Yamaguchi (JP)

(73) Assignee: Mitsui Chemicals, Inc., Tokyo (JP)

( * ) Notice: Subject to any disclaimer, the term of this patent is extended or adjusted under 35 U.S.C. 154(b) by 88 days.

(21) Appl. No.: 10/695,831

(22) Filed: Oct. 30, 2003

(65) Prior Publication Data
US 2005/0131171 A1 Jun. 16, 2005

(30) Foreign Application Priority Data
Oct. 30, 2002 (JP) .............................. 2002-316579

(51) Int. Cl.
*C08F 4/64* (2006.01)
*C08F 4/6392* (2006.01)

(52) U.S. Cl. ....................... 526/160; 526/133; 526/134; 526/165; 526/348

(58) Field of Classification Search ................ 526/160, 526/165, 348, 133, 134
See application file for complete search history.

(56) References Cited

U.S. PATENT DOCUMENTS

| | | | |
|---|---|---|---|
| 5,036,034 A | | 7/1991 | Ewen |
| 5,436,305 A | * | 7/1995 | Alt et al. ..................... 526/160 |
| 5,571,880 A | * | 11/1996 | Alt et al. ..................... 526/160 |
| 6,403,734 B1 | * | 6/2002 | Alt et al. ..................... 526/160 |
| 6,469,188 B1 | | 10/2002 | Miller et al. |

FOREIGN PATENT DOCUMENTS

| | | |
|---|---|---|
| CN | 1051735 A | 5/1991 |
| JP | 59-210905 | 11/1984 |
| JP | 61-236804 | 10/1986 |
| JP | 01-203410 | 8/1989 |
| JP | 02-173104 | 7/1990 |
| JP | 04-069394 | 3/1992 |
| JP | 06-049129 | 2/1994 |
| JP | 08-239414 | 9/1996 |
| JP | 10-226695 A | 8/1998 |

OTHER PUBLICATIONS

Walter Kaminsky et al. "Polymerization of Propene and Butene with a Chiral Zirconocene and Methylalumoxane as Cocatalyst", Angew. Chem. Int. Ed. Engl. 1985, pp. 507-508, vol. 24, No. 6, VCH Verlagsgesellschaft mbH, Weinheim, Germany.

John A. Ewen et al., "Syndiospecific Propylene Polymerization with Group 4 Metallocenes", J. Am. Chem. Soc., 1988, pp. 6255-6256, vol. 110, American Chemical Society.

Min Hyung Lee et al. "Ethylene-Bridged Pseudo-$C_s$ Symmetric *Ansa*-Zirconocene Complexed: synthesis, Structures and Propylene Polymerization Behavior", Journal of Organometallic Chemistry, 1998, pp. 37-47, vol. 561, Elsevier Science S.A., Holland.

Il Kim et al., "Copolymerization of Ethylene and 1-Decene by Metallocenes: Direct Comparison of $Me_2C(Cp)(Flu)ZrMe_2$", Polymer Engineering and Science, 2001, pp. 899-907, vol. 41, No. 6.

* cited by examiner

*Primary Examiner*—Caixia Lu
(74) *Attorney, Agent, or Firm*—Buchanan Ingersoll & Rooney PC

(57) ABSTRACT

The present invention provides a process for preparing a low molecular weight olefin (co)polymer having a narrow molecular weight distribution with high productivity, by polymerizing or copolymerizing an olefin in the presence of an olefin polymerization catalyst comprising (A) a specific Group 4 transition metal compound, and (B) at least one compound selected from the group consisting of (B-1) an organometallic compound, (B-2) an organoaluminum compound, (B-3) an organoaluminum oxy-compound, and (B-4) a compound which reacts with the Group 4 transition metal compound (A) to form an ion pair; and compounds useful in that process.

7 Claims, No Drawings

PROCESS FOR PREPARING LOW MOLECULAR WEIGHT OLEFIN (CO)POLYMER AND POLYMERIZATION CATALYST USED THEREFOR

FIELD OF THE INVENTION

The present invention relates to a process for preparing a low molecular weight olefin (co)polymer and a polymerization catalyst used therefor, more particularly, a process for preparing a low molecular weight olefin (co)polymer having a narrow molecular weight distribution with high productivity and a polymerization catalyst used therefor.

BACKGROUND ART

An olefin low molecular weight polymer such as a polyethylene wax is used in applications such as a pigment dispersant, a resin processing aid, a printing ink additive, a paint additive, a rubber processing aid and a fiber treating agent. In addition, an olefin low molecular weight polymer is also used in a releasing agent for toner. Recently, from a viewpoint of energy saving, a low temperature fixing toner is sought, and an appearance of a wax having better release characteristics at a low temperature, that is, a wax having a lower melting point with the same composition and the same molecular weight is desired.

As a process for preparing such an olefin low molecular weight polymer, conventionally, a titanium catalyst has been usually used industrially. However, although the catalyst has an advantage that, in case of using the catalyst system, the yield of the low molecular weight polymer per unit amount of the catalyst is high, and the productivity is high, it also has a technical challenge that it is necessary to maintain a high hydrogen partial pressure in the gaseous phase in the polymerization system and, as a result, a large amount of alkanes as side products are produced.

Furthermore, the molecular weight distribution of the resulting low molecular weight polymer is wide and, in particular, since the low molecular weight polymer having a molecular weight of 1000 or smaller is greatly sticky, it is difficult to use it in the aforementioned applications without removing the low-molecular weight fraction.

As a method for solving these challenges, Japanese Patent Laid-Open Publication No. 210905/1984 proposes a process for preparing a low molecular weight polymer using a vanadium catalyst. This publication describes that a low molecular weight polymer having a narrow molecular weight distribution can be prepared under a low hydrogen partial pressure, as compared with that prepared using a titanium catalyst. However, the molecular weight distribution is not necessarily sufficient. In addition, Japanese Patent Laid-Open Publication No. JP-A No. 78462/1985 proposes a process for preparing an ethylene wax, comprising the step of polymerizing ethylene or copolymerizing ethylene with an α-olefin, in the presence of a metallocene catalyst comprising (A) a compound of a transition metal selected from the group consisting of Group 4 elements, Group 5 elements and Group 6 elements of the periodic table and (B) an aluminoxane. According to this process, an ethylene wax having a narrow molecular weight distribution can be prepared, but a process for preparing an ethylene wax having further excellent productivity is desired.

Furthermore, Japanese Patent Laid-Open Publication No. 203410/1989 and Japanese Patent Laid-Open Publication No. 49129/1994 describe preparation of an ethylene wax using a metallocene catalyst comprising a metallocene and an aluminoxane. However, in these methods, the productivity is not necessarily sufficient. When a polymerizing temperature is raised, it becomes easy to remove the polymerization heat, and the productivity can be improved, but there is a challenge that a yield of a low molecular weight polymer per unit weight of a catalyst is lowered.

Japanese Patent Laid-Open Publication No. 239414/1996 has already proposed a process for preparing an ethylene wax, comprising the step of (co)polymerizing ethylene in the presence of an olefin polymerization catalyst comprising (A) a Group 4B transition metal compound containing a ligand having a cyclopentadienyl skeleton, (B) a compound which reacts with the (A) to form an ion pair, and (C) an organoaluminum compound. According to this process, an ethylene wax having a narrow molecular weight distribution can be prepared at high production efficiency, but a process for preparing an ethylene wax further excellent in the productivity and the quality is desired.

SUMMARY OF THE INVENTION

The present inventors intensively studied in order to solve the aforementioned Challenges in the background art and, as a result, have found that a low molecular weight olefin (co)polymer having a narrow molecular weight distribution is obtained with high productivity by polymerizing or copolymerizing an olefin in the presence of an olefin polymerization catalyst containing a specific transition metal compound.

Also, we have found that, in the case that the main monomer is ethylene, a low molecular weight olefin (co) polymer having a narrow molecular weight distribution, a low melting point and a low intrinsic viscosity is obtained with very high productivity when the aforementioned (co) polymerization is performed at a temperature of 100° C. or higher.

The present invention provides a process for preparing a low molecular weight olefin (co)polymer having a narrow molecular weight distribution with high productivity.

The present invention provides a process for preparing a low molecular weight olefin (co)polymer having a narrow molecular weight distribution with the high productivity, comprising a step of polymerizing or copolymerizing an olefin in the presence of a polymerization catalyst containing a specific transition metal compound.

The present invention provides an olefin polymerization catalyst that can prepare a low molecular weight olefin (co)polymer having a narrow molecular weight distribution with high productivity in the presence of a specific transition metal compound.

Furthermore, the present invention provides a novel transition metal compound suitable as a component for polymerizing an olefin.

More specifically, a process for preparing a low molecular weight olefin (co)polymer having a narrow molecular weight distribution with high productivity in accordance with the present invention is:

a process for preparing a low molecular weight olefin(co) polymer by polymerizing or copolymerizing an olefin in the presence of an olefin polymerization catalyst comprising:

(A) a Group 4 transition metal compound represented by the following general formula (1) and, (B) at least one compound selected from the group consisting of (B-1) an organometallic compound, (B-2) an organoaluminum compound, (B-3) an organoaluminum oxy-compound, and (B-4) a compound which reacts with the Group 4 transition metal compound (A) to form an ion pair;

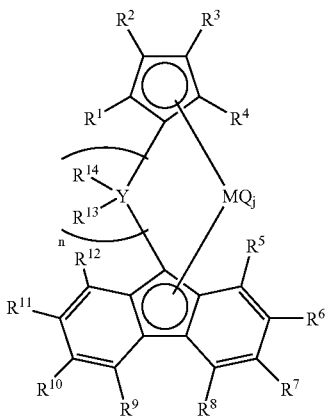

(1)

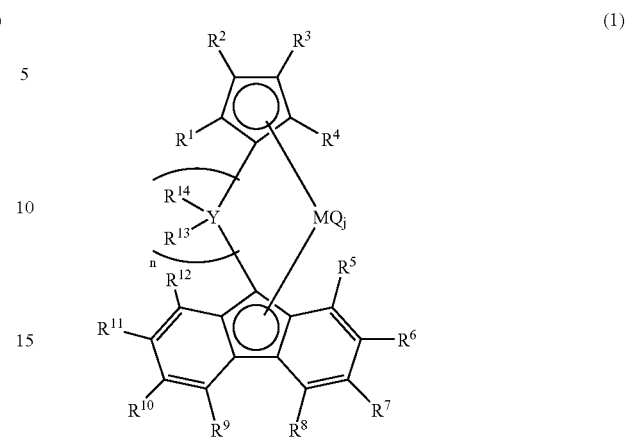

(1)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may be the same or different, and are independently selected from the group consisting of hydrogen, a hydrocarbon group and a silicon-containing group; each adjacent pair of substituents $R^1$ to $R^{14}$ may be taken together to form a ring; M is Ti, Zr or Hf; Y is a Group 14 atom; each Q is independently selected from the group consisting of: a halogen, a hydrocarbon group, a neutral conjugated or non-conjugated diene having 10 or fewer carbon atoms, an anionic ligand, and a neutral ligand that can be coordinated with a lone electron pair; n is an integer of from 2 to 4; and j is an integer of from 1 to 4; wherein an intrinsic viscosity [η] of the low molecular weight olefin (co)polymer measured in decalin at 135° C. is 0.6 dl/g or less.

In the present invention, in particular, when ethylene is a main monomer, the polymerization or copolymerization of an olefin at a polymerizing temperature of 100° C. or higher is a preferable embodiment of the aforementioned polymerizing process.

DETAILED DESCRIPTION OF PREFERRED EMBODIMENTS

Preferred embodiments of the process for preparing a low molecular weight olefin (co)polymer and the polymerization catalyst used therefor in accordance with the present invention will be specifically explained below.

As used herein, the term "polymerization" includes not only homopolymerization but also copolymerization, and the term "polymer" includes not only a homopolymer but also a copolymer.

First, respective components constituting an olefin polymerization catalyst used in the present invention will be explained.

(A) Group 4 Transition Metal Compound

Among components constituting an olefin polymerization catalyst used in the present invention, (A) a Group 4 transition metal compound is represented by the following general formula (1).

In the formula, $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may be the same or different, and are independently selected from the group consisting of hydrogen, a hydrocarbon group and a silicon-containing group; each adjacent pair of substituents $R^1$ to $R^{14}$ may be taken together to form a ring; M is Ti, Zr or Hf; Y is a Group 14 atom; each Q is independently selected from the group consisting of: a halogen, a hydrocarbon group, a neutral conjugated or non-conjugated diene having 10 or fewer carbon atoms, an anionic ligand, and a neutral ligand that can be coordinated with a lone electron pair; n is an integer of from 2 to 4; and j is an integer of from 1 to 4.

In the above formula (1), the hydrocarbon group that may constitute $R^1$ to $R^{14}$ is preferably an alkyl group having 1 to 20 carbon atoms, an arylalkyl group having 7 to 20 carbon atoms, an aryl group having 6 to 20 carbon atoms, or an alkylaryl group having 7 to 20 carbon atoms, and may contain one or more ring structures.

Examples thereof include methyl, ethyl, n-propyl, isopropyl, 2-methylpropyl, 1,1-dimethylpropyl, 2,2-dimethylpropyl, 1,1-diethylpropyl, 1-ethyl-1-methylpropyl, 1,1,2,2-tetramethylpropyl, sec-butyl, tert-butyl, 1,1-dimethylbutyl, 1,1,3-trimethylbutyl, neopentyl, cyclohexylmethyl, cyclohexyl, 1-methyl-1-cyclohexyl, 1-adamantyl, 2-adamatyl, 2-methyl-2-adamantyl, menthyl, norbornyl, benzyl, 2-phenylethyl, 1-tetrahydronaphthyl, 1-methyl-1-tetrahydronaphthyl, phenyl, naphthyl, tolyl and so on.

In the above formula (1), the silicon-containing group is preferably an alkyl- or arylsilyl group having 1 to 4 silicon atoms and 3 to 20 carbon atoms, and examples thereof include trimethylsilyl, tert-butyldimethylsilyl, triphenylsilyl and so on.

In the present invention, $R^1$ to $R^{14}$ in the above formula (1) are selected from the group consisting of hydrogen, a hydrocarbon group and a silicon-containing group, and may be the same or different from each other. Preferable examples of a hydrocarbon group and a silicon-containing group include those as described above.

Each adjacent pair of substituents $R^1$ to $R^{14}$ on a cyclopentadienyl ring in the above formula (1) may be taken together to form a ring.

M in the formula (1) is a Group 4 element of periodic table, that is, zirconium, titanium or hafnium, preferably zirconium.

Y is a Group 14 atom, preferably a carbon atom or a silicon atom, and n is an integer of from 2 to 4, preferably from 2 or 3, particularly preferably 2.

Each Q is independently selected from the group consisting of a halogen, a hydrocarbon group, a neutral conjugated or non-conjugated diene having 10 or fewer carbon atoms, an anionic ligand and a neutral ligand that can be coordinated with a lone electron pair. When Q is a hydrocarbon group, it is more preferably a hydrocarbon group having 1 to 10 carbon atoms.

Examples of the halogen include fluorine, chlorine, bromine and iodine, and examples of the hydrocarbon group include methyl, ethyl, n-propyl, isopropyl, 2-methylpropyl, 1,1-dimethylpropyl, 2,2-dimethylpropyl, 1,1-diethylpropyl, 1-ethyl-1-methylpropyl, 1,1,2,2-tetramethylpropyl, sec-butyl, tert-butyl, 1,1-dimethylbutyl, 1,1,3-trimethylbutyl, neopentyl, cyclohexylmethyl, cyclohexyl, 1-methyl-1-cyclohexyl and so on. Examples of the neutral conjugated or non-conjugated diene having 10 or fewer carbon atoms include s-cis- or s-trans-$\eta^4$-1,3-butadiene, s-cis- or s-trans-$\eta^4$-1,4-diphenyl-1,3-butadiene, s-cis- or s-trans-$\eta^4$-3-methyl-1,3-pentadiene, s-cis- or s-trans-$\eta^4$-1,4-dibenzyl-1,3-butadiene, s-cis- or s-trans-$\eta^4$-2,4-hexadiene, s-cis- or s-trans-$\eta^4$-1,3-pentadiene, s-cis- or s-trans-$\eta^4$-1,4-ditolyl-1,3-butadiene, s-cis- or s-trans-$\eta^4$-1,4-bis(trimethylsilyl)-1,3-butadiene and so on. Examples of the anionic ligand include an alkoxy group such as methoxy, tert-butoxy and phenoxy; a carboxylate group such as acetate and benzoate; a sulfonate group such as mesylate and tosylate; and so on. Examples of the neutral ligand which can be coordinated with a lone electron pair include an organophosphorus compound such as trimethylphosphine, triethylphosphine, triphenylphosphine and diphenylmethylphosphine, and ethers such as tetrahydrofuran, diethyl ether, dioxane, 1,2-dimethoxyethane and so on. When j is an integer of 2 or larger, each Q may be the same or different from any other Q.

In the formula (1), the compound has more than one (2 to 4) Y. Each Y may be the same or different from any other Y. Plural $R^{13}$'s and plural $R^{14}$'s which bind to Y may be the same or different from each other. For example, plural $R^{13}$'s which bind to the same Y may be different, or plural $R^{13}$'s which bind to different Y's may be the same. Further, $R^{13}$'s or $R^{14}$'s may be taken together to form a ring.

Preferable examples of a Group 4 transition metal compound represented by the formula (1) include a compound represented by the following formula (1'):

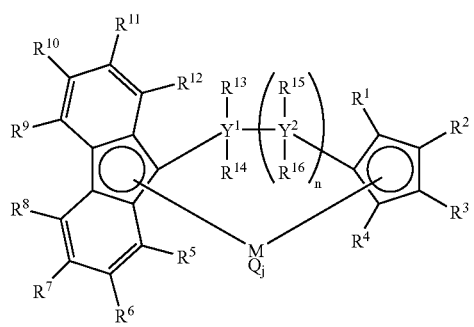

(1')

In the formula (1') $R^1$, $R^2$, $R^3$, $R^4$, $R^5$, $R^6$, $R^7$, $R^8$, $R^9$, $R^{10}$, $R^{11}$, and $R^{12}$ may be the same or different, and are independently selected from the group consisting of a hydrogen atom, a hydrocarbon group and a silicon-containing group; each of $R^{13}$, $R^{14}$, $R^{15}$ and $R^{16}$ is independently a hydrogen atom or a hydrocarbon group; n is an integer of from 1 to 3 and, when n is 1, not all of $R^1$ to $R^{16}$ are hydrogen atoms and may be the same or different from each other. Each adjacent pair of substituents $R^5$ to $R^{12}$ may be taken together to form a ring; $R^{13}$ and $R^{15}$ may be taken together to form a ring, or the pair of $R^{13}$ and $R^{15}$ and the pair of $R^{14}$ and $R^{16}$ may be taken together to form rings simultaneously; $Y^1$ and $Y^2$ may be the same or different from each other, and each of them is a Group 14 atom; M is Ti, Zr or Hf; each Q is independently selected from the group consisting of a halogen, a hydrocarbon group, an anionic ligand and a neutral ligand that can be coordinated with a lone electron pair; and j is an integer of from 1 to 4.

In the Group 4 transition compound represented by the formula (1'), an order arranging $Y^1$ and singular or plural $Y^{2}$'(s) may be arbitrarily selected in spite of the above formula.

The Group 4 transition metal compound represented by the above formula (1') is a novel compound useful for forming an olefin polymerization catalyst.

Examples of Group 4 transition metal compounds represented by the above general formula (1) or (1'), which is a preferable example thereof, will be shown below, but the scope of the present invention is not limited by them. A ligand structure of the Group 4 transition metal compounds represented by the general formula (1) or (1') except for the part of $MQ_j$ (metal part) is divided into three parts of Cp (cyclopentadienyl ring part), Bridge (bridging part) and Flu (fluorenyl ring part) for the convenience of expression. Examples of respective structures of the parts and examples of a ligand structure in a combination thereof will be shown below. In examples of Cp and Bridge, points represented by black spots (•) represent points where they are connected with Bridge and Cp, respectively.

[Examples of CP]

a1

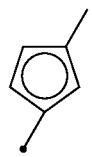
a2

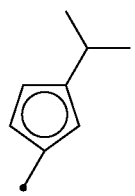
a3

-continued
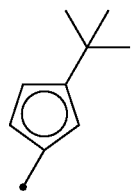
a4
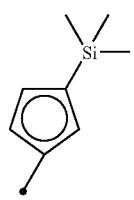
a5
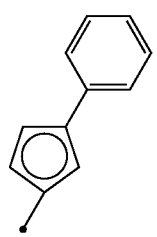
a6
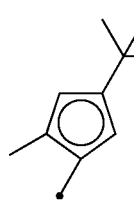
a7
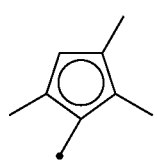
a8
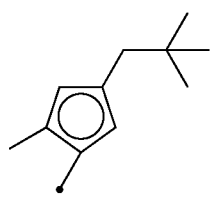
a9
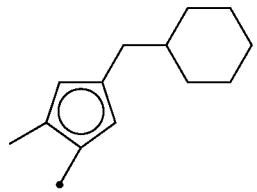
a10
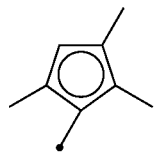
a11
-continued
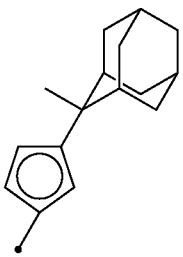
a12
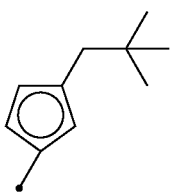
a13
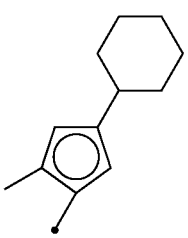
a14
[Examples of Bridge]
b1
b2
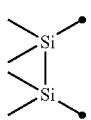
b3
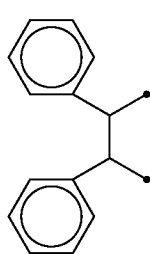
b4

-continued
b5 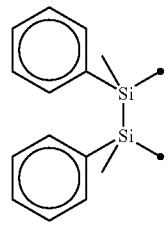
b6 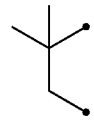
b7 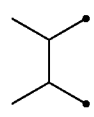
b8 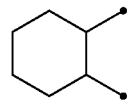
b9 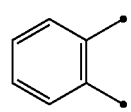
b10 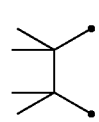
b11 
b12 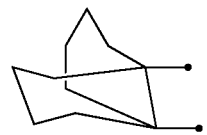
b13 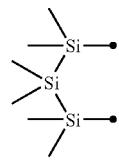
b14 
b15 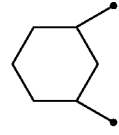
-continued
b16 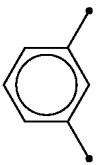
[Examples of Flu]
C1 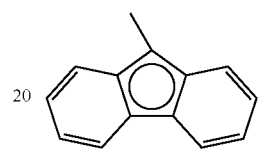
C2 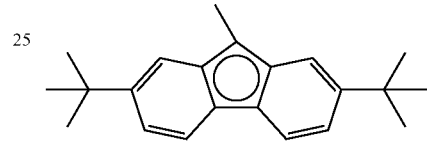
C3 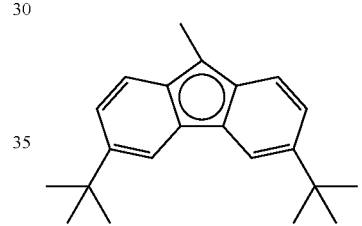
C4 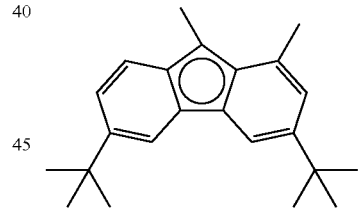
C5 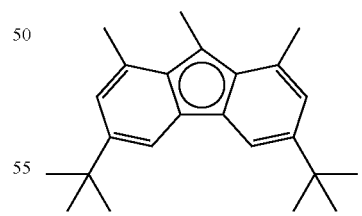
C6 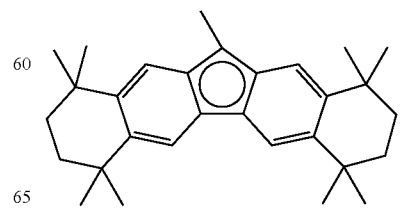

-continued

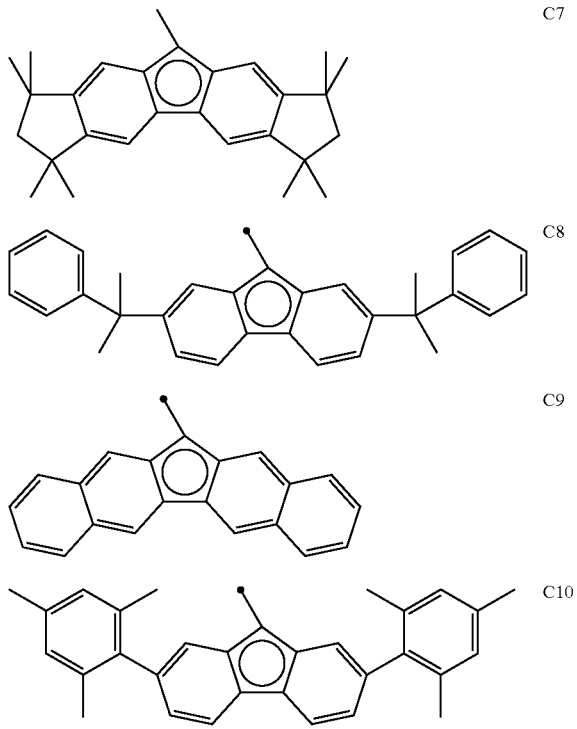

The above-exemplified Cp (cyclopentadienyl ring part), Bridge (bridging part) and Flu (fluorenyl ring part) may be combined arbitrarily, and each combination of selected Cp, Bridge and Flu is a specific example of the ligand structure. For example, when a ligand structure is a combination of a1-b1-c2, and $MQ_j$ as a metal part is $ZrCl_2$, the following metallocene compound is exemplified.

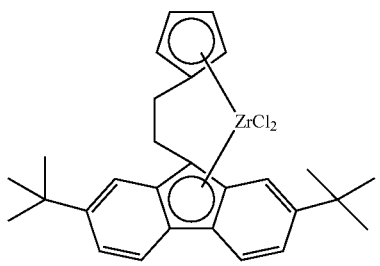

Examples of $MQ_j$ in the above formula (1) include $ZrCl_2$, $ZrBr_2$, $ZrMe_2$, $ZrEt_2$, $Zr(n-Pr)_2$, $ZrMeEt$, $ZrClMe$, $ZrBrMe$, $Zr(s-trans-\eta^4-1,3-butadiene)$, $Zr(s-trans-\eta^4-1,4-Ph_2-1,3-butadiene)$, $Zr(s-trans-\eta^4-3-Me-1,3-pentadiene)$, $Zr(s-trans-\eta^4-1,4-(CH_2Ph)_2-1,3-butadiene)$, $Zr(s-trans-\eta^4-2,4-hexadiene)$, $Zr(s-trans-\eta^4-1,3-pentadiene)$, $Zr(s-trans-\eta^4-1,4-(p-tol)_2-1,3-butadiene)$, $Zr(s-trans-\eta^4-1,4-(SiMe_3)_2-1,3-butadiene)$, $Zr(s-cis-\eta^4-1,3-butadiene)$, $Zr(s-cis-\eta^4-1,4-Ph_2-1,3-butadiene)$, $Zr(s-cis-\eta^4-3-Me-1,3-pentadiene)$, $Zr(s-cis-\eta^4-1,4-(CH_2Ph)_2-1,3-butadiene)$, $Zr(s-cis-\eta^4-2,4-hexadiene)$, $Zr(s-cis-\eta^4-1,3-pentadiene)$, $Zr(s-cis-\eta^4-1,4-(p-tol)_2-1,3-butadiene)$, $Zr(s-cis-\eta^4-1,4-(SiMe_3)_2-1,3-butadiene)$, $Zr(OTs)_2$, $Zr(OMs)_2$, and $Zr(OTf)_2$, and compounds in which the transition metals, zirconium, of the compounds described above are replaced with titanium or hafnium.

(B-1) Organometallic Compound

As the (B-1) organometallic compound used in the present invention, specifically, the following organometallic compound is used.

Dialkyl compound of a Group 2 or Group 12 metal of the periodic table represented by the formula:

$$R^a R^b M^3$$

(In the formula, $R^a$ and $R^b$ may be the same or different from each other, and represent a hydrocarbon group having 1 to 15, preferably 1 to 4 carbon atoms, and $M^3$ is Mg, Zn or Cd.) These organometallic compounds (B-1) may be used alone or in combination of two or more of them.

(B-2) Organoaluminum Compound

Examples of the (B-2) organoaluminum compound constituting the olefin polymerization catalyst include organoaluminum compounds represented by the following general formula (7), and alkylated complexes of a Group 1 metal and aluminum represented by the following general formula (8). Organoaluminum compounds represented by:

$$R^a_m Al(OR^b)_n H_p X_q \quad (7)$$

(In the formula, $R^a$ and $R^b$ may be the same or different from each other, and represent a hydrocarbon group having 1 to 15, preferably 1 to 4 carbon atoms, X represents a halogen atom, m is a number of $0<m\leq3$, n is a number of $0\leq n<3$, p is a number of $0\leq p<3$, q is a number of $0\leq q\leq3$, and m+n+p+q=3.) Examples of such compounds include trimethylaluminum, triethylaluminum, triisobutylaluminum, and diisobutylaluminum hydride.

Alkylated complexes of a Group 1 metal of the periodic table and aluminum represented by:

$$M^2 AlR^a_4 \quad (8)$$

(In the formula, $M^2$ represents Li, Na or K, and $R^a$ represents a hydrocarbon group of 1 to 15, preferably 1 to 4 carbon atoms.) Examples of such compounds include $LiAl(C_2H_5)_4$, and $LiAl(C_7H_{15})_4$.

Examples of the organoaluminum compound represented by the above general formula (7) include compounds represented by the following formula (9), (10), (11) or (12).

$$R^a_m Al(Or^b)_{3-m} \quad (9)$$

(In the formula $R^a$ and $R^b$ may be the same or different from each other, and each represents a hydrocarbon group having 1 to 15, preferably 1 to 4 carbon atoms, and m is preferably a number of $1.5\leq m\leq3$.)

$$R^a_m AlX_{3-m} \quad (10)$$

(In the formula, $R^a$ represents a hydrocarbon group having 1 to 15, preferably 1 to 4 carbon atoms, X represents a halogen atom, and m is preferably such a number that; $0<m<3$.)

$$R^a_m AlH_{3-m} \quad (11)$$

(In the formula, $R^a$ represents a hydrocarbon group having 1 to 15, preferably 1 to 4 carbon atoms, m is preferably such a number that; $2\leq m<3$.)

$$R^a_m Al(OR^b)_n Xq \quad (12)$$

(In the formula, $R^a$ and $R^b$ may be the same or different from each other, and represent a hydrocarbon group having 1 to 15, preferably 1 to 4 carbon atoms, X represents a halogen atom, m is a number of $0<m\leq 3$, n is a number of $0\leq n<3$, q is a number of $0\leq q<3$, and m+n+q=3.)

More specific examples of aluminum compounds represented by the above general formula (9), (10), (11) or (12) include tri-n-alkylaluminum such as trimethylaluminum, triethylaluminum, tri-n-butylaluminum, tripropylaluminum, tripentylaluminum, trihexylaluminum, trioctylaluminum, and tridecylaluminum; tri-branched alkylaluminum such as triisopropylaluminum, triisobutylaluminum, tri-sec-butylaluminum, tri-tert-butylaluminum, tri-2-methylbutylaluminum, tri-3-methylbutylaluminum, tri-2-methylpentylaluminum, tri-3-methylpentylaluminum, tri-4-methylpentylaluminum, tri-2-methylhexylaluminum, tri-3-methylhexylaluminum, and tri-2-ethylhexylaluminum; tricycloalkylaluminum such as tricyclohexylaluminum, and tricyclooctylaluminum; triarylaluminum such as triphenylaluminum, and tritolylaluminum; dialkylaluminum hydride such as diisopropylaluminum hydride, and diisobutylaluminum hydride; alkenylaluminum such as isoprenylaluminum represented by the general formula $(i-C_4H_9)_xAl_y(C_5H_{10})_z$ (wherein x, y and z are a positive number, and $z\leq 2x$); alkylaluminum alkoxide such as isobutylaluminum methoxide, isobutylaluminum ethoxide, and isobutylaluminum isopropoxide; dialkylaluminum alkoxide such as dimethylaluminium methoxide, diethylaluminium ethoxide, and dibutylaluminiumbutoxide; alkylaluminium sesquialkoxide such as ethylaluminium sesquiethoxide, and butylaluminium sesquibutoxide; partially alkoxylated alkylaluminium having the average composition represented by the general formula $R^a_{2.5}Al(OR^b)_{0.5}$; alkylaluminium aryloxide such as diethylaluminum phenoxide, diethylaluminium (2,6-di-t-butyl-4-methylphenoxide), ethylaluminium bis(2,6-di-t-butyl-4-methylphenoxide), diisobutylaluminum (2,6-di-t-butyl-4-methylphenoxide), and isobutylaluminum bis(2,6-di-t-butyl-4-methylphenoxide); dialkylaluminum halide such as dimethylaluminum chloride, diethylaluminum chloride, dibutylaluminum chloride, diethylaluminum bromide, and diisobutylaluminum chloride; alkylaluminum sesquihalide such as ethylaluminum sesquichloride, butylaluminum sesquichloride, and ethylaluminum sesquichloride; partially halogenated alkylaluminum such as alkylaluminum dihalide such as ethylaluminum dichloride, propylaluminum dichloride, and butylaluminum dibromide; dialkylaluminum hydride such as diethylaluminum hydride, and dibutylaluminum hydride; other partially hydrogenated alkylaluminum such as alkylaluminum dihydride such as ethylaluminum dihydride, and propylaluminum dihydride; partially alkoxylated and halogenated alkylaluminum such as ethylaluminum ethoxychloride, butylaluminum butoxychloride, and ethylaluminum ethoxybromide; and so on.

Alternatively, compounds similar to the compounds represented by the above general formula (7) may be used, and examples thereof include organoaluminum compounds in which two or more aluminum compounds are connected through a nitrogen atom. Specific examples of such the compound include $(C_2H_5)_2AlN(C_2H_5)Al(C_2H_5)_2$.

Examples of the compounds represented by the above general formula (8) include $LiAl(C_2H_5)_4$, and $LiAl(C_7H_{15})_4$.

Alternatively, a compound from which the above organoaluminum compound is formed in the polymerization system, for example, a combination of a halogenated aluminum and an alkyllithium, or a combination of a halogenated aluminum and an alkylmagnesium may be used.

Among them, organoaluminum compounds are preferable.

Organoaluminum compounds represented by the above formula (7), or alkylated complexes of a Group 1 metal and aluminum represented by the above formula (8) may be used alone or in combination of two or more of them.

(B-3) Organoaluminum Oxy-Compound (B-3) The organoaluminum oxy-compound used in the present invention may be the conventionally known aluminoxane, or may be the benzene-insoluble organoaluminum oxy-compound exemplified in Japanese Patent Laid-Open Publication No. 78687/1990.

The conventionally known aluminoxane can be prepared, for example, by the following method, and is usually obtained as a solution in a hydrocarbon solvent.

(1) A method of adding an organoaluminum compound such as trialkylaluminum to a suspension of a compound having absorbed water or a salt containing water of crystallization, for example, magnesium chloride hydrate, copper sulfate hydrate, aluminum sulfate hydrate, nickel sulfate hydrate, or cereus chloride hydrate in a hydrocarbon medium, to react the organoaluminum compound with the absorbed water or the water of crystallization.

(2) A method of reacting water, ice or water vapor directly with an organoaluminum compound such as trialkylaluminum in a medium such as benzene, toluene, ethylether, or tetrahydrofuran.

(3) A method of reacting an organoaluminum compound such as trialkylaluminum with an organotin oxide such as dimethyltin oxide, and dibutyltin oxide in a medium such as decane, benzene, or toluene.

The aluminoxane may contain a small amount of an organometallic component. A solvent or an unreacted organoaluminum compound may be distilled off from a recovered solution of the aluminoxane, and the aluminoxane may be redissolved in a solvent or suspended in a poor solvent for aluminoxane.

Examples of an organoaluminum compound used upon preparation of aluminoxane include the same organoaluminum compounds as those exemplified as the organoaluminum compound of the above (B-2).

Among them, trialkylaluminum, and tricycloalkylaluminum are preferable, and trimethylaluminum is particularly preferable.

The aforementioned organoaluminum compounds may be used alone or in combination of two or more of them.

In addition, as the benzene-insoluble organoaluminum oxy-compound used in the present invention, those compounds in which an Al component soluble in benzene at 60° C. is usually 10% or smaller, preferably 5% or smaller, particularly preferably 2% or smaller in terms of Al atom, that means, those compounds which is insoluble or hardly soluble in benzene are preferable. These organoaluminum oxy-compounds (B-3) are used alone or in combination of two or more of them.

Aluminoxane prepared from trimethylaluminum is called methylaluminoxane or MAO, and is a compound which is used particularly frequently.

Examples of a solvent used for preparing aluminoxane include aromatic hydrocarbons such as benzene, toluene, xylene, cumene, and cymene; aliphatic hydrocarbons such as pentane, hexane, heptane, octane, decane, dodecane, hexadecane, and octadecane; alicyclic hydrocarbons such as cyclopentane, cyclohexane, cyclooctane, and methylcyclopentane; petroleum fractions such as gasoline, kerosene, and gas oil; and halides of the aforementioned aromatic hydrocarbons, aliphatic hydrocarbons, and alicyclic hydrocarbons, inter alia, chlorinated or brominated hydrocarbon solvents. Furthermore, ethers such as ethyl ether and tetrahydrofuran may be used. Among these solvents, aromatic hydrocarbons and aliphatic hydrocarbons are particularly preferable.

Examples of the organoaluminum oxy-compound used in the present invention also include organoaluminum oxy-compounds represented by the following formula (13).

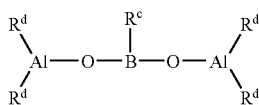
(13)

(In the formula, $R^c$ represents a hydrocarbon group having 1 to 10 carbon atoms, and each $R^d$ independently represents a hydrogen atom, a halogen atom or a hydrocarbon group having 1 to 10 carbon atoms.)

The organoaluminum oxy-compound containing boron represented by the above formula (13) can be prepared by reacting alkylboronic acid represented by the following formula (14) and an organoaluminum compound at a temperature of from −80° C. to room temperature for from 1 minute to 24 hours in an inert solvent under an inert gas atmosphere.

$$R^cB(OH)_2 \tag{14}$$

(In the formula, $R^c$ is as defined above.)

Examples of alkylboronic acid represented by the above general formula (14) include methylboronic acid, ethylboronic acid, isopropylboronic acid, n-propylboroinc acid, n-butylboronic acid, isobutylboronic acid, n-hexylboronic acid, cyclohexylboronic acid, phenylboronic acid, 3,5-difluorophenylboronic acid, pentafluorophenylboronic acid, and 3,5-bis(trifluoromethyl)phenylboronic acid. Among them, methylboronic acid, n-butylboronic acid, isobutylboronic acid, 3,5-difluorophenylboronic acid, and pentafluorophenylboronic acid are preferable. These are used alone or in combination of two or more of them.

Examples of an organoaluminum compound to be reacted with such the alkylboronic acid include the same organoaluminum compounds as those exemplified as the organoaluminum compound represented by the above formula (7) or (8).

Among them, trialkylaluminums, and tricycloalkylaluminums are preferable, and trimethylaluminum, triethylaluminum, and triisobutylaluminum are particularly preferable. These are used alone or in combination of two or more of them.

(B-4) Compound which Reacts with the Aforementioned Group 4 Transition Metal Compound (A) to Form an Ion Pair Examples of the compound (B-4) which reacts with the aforementioned Group 4 transition metal compound (A) to form an ion pair include Lewis acids, ionic compounds, borane compounds and carborane compounds described in Japanese Patent Laid-Open Publication No. 1-501950/1989, Japanese Patent Laid-Open Publication No. 502036/1989, Japanese Patent Laid-Open Publication No. 179005/1991, Japanese Patent Laid-Open Publication No. 179006/1991, Japanese Patent Laid-Open Publication No. 207703/1991, Japanese Patent Laid-Open Publication No. 207704/1991, and U.S. Pat. No. 5,321,106.

Examples of the Lewis acid include compounds represented by $BR_3$ (R is a phenyl group optionally having a substituent such as fluorine, a methyl group, and a trifluoromethyl group, fluorine or an alkyl group such as methyl group or isobutyl group.) such as trifluoroboron, triphenylboron, tris(4-fluorophenyl)boron, tris(3,5-difluorophenyl)boron, tris(4-fluoromethylphenyl)boron, tris(pentafluorophenyl)boron, tris(p-tolyl)boron, tris(o-tolyl)boron, tris(3,5-dimethylphenyl)boron, trimethylboron, and triisobutylboron.

Examples of the ionic compounds include compounds represented by the following formula (2):

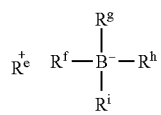
(2)

In the formula, examples of $R^{e+}$ include $H^+$, carbenium cation, oxonium cation, ammonium cation, phosphonium cation, cyclopentyltrienyl cation, and ferrocenium cation having a transition metal. Each of $R^f$, $R^g$, $R^h$ and $R^i$ may be the same or different from each other, and is an organic group, preferably an aryl group or a substituted aryl group.

Examples of the carbenium cation include tri-substituted carbenium cations such as triphenylcarbenium cation, tris (methylphenyl)carbenium cation, and tris(dimethylphenyl) carbenium cation.

Examples of the ammonium cation include trialkylammonium cations such as trimethylammonium cation, triethylammonium cation, tri(n-propyl)ammonium cation, triisopropylammonium cation, tri(n-butyl)ammonium cation, and triisobutyl ammonium cation; N,N-dialkylanilinium cations such as N,N-dimethylaniliniumcation, N,N-diethylaniliniumcation, and N,N-2,4,6-pentamethylanilinium cation; and dialkylammonium cations such as diisopropylammonium cation, and dicyclohexylammonium cation.

Examples of the phosphonium cation include triarylphosphonium cations such as triphenylphosphonium cation, tris (methylphenyl)phosphonium cation, and tris(dimethylphenyl)phosphonium cation.

Among the examples described above, as $R^e$, carbenium cations and ammonium cations are preferable, and triphenylcarbenium cation, N,N-dimethylanilinium cation and N,N-diethylanilinium cation are particularly preferable.

Examples of a carbenium salt include triphenylcarbenium tetraphenylborate, triphenylcarbenium tetrakis(pentafluorophenyl)borate, triphenylcarbenium tetrakis(3,5-ditrifluoromethylphenyl)borate, tris(4-methylphenyl)carbenium tetrakis(pentafluorophenyl)borate, and tris(3,5-dimethylphenyl)carbenium tetrakis(pentafluorophenyl) borate.

Examples of an ammonium salt include a trialkyl-substituted ammonium salt, an N,N-dialkylanilinium salt, and a dialkylammonium salt.

Examples of a tri-alkyl substituted ammonium salt include triethylammonium tetraphenylborate, tripropylammonium tetraphenylborate, tri(n-butyl)ammonium tetraphenylborate, trimethylammonium tetrakis(p-tolyl)borate, trimethylammonium tetrakis(o-tolyl)borate, tri(n-butyl) ammonium tetrakis(pentafluorophenyl)borate, triethylammonium tetrakis(pentafluorophenyl)borate, tripropylammonium tetrakis(pentafluorophenyl)borate, tripropylammonium tetrakis(2,4-dimethylphenyl)borate, tri (n-butyl)ammonium tetrakis(3,5-dimethylphenyl)borate, tri (n-butyl)ammonium tetrakis(4-trifluoromethylphenyl)borate, tri(n-butyl)ammonium tetrakis(3,5-ditrifluoromethylphenyl)borate, tri(n-butyl)ammonium tetrakis(o-tolyl)borate, dioctadecylmethylammonium tetraphenylborate, dioctadecylmethylammonium tetrakis(p-tolyl)borate, dioctadecylmethylammonium tetrakis(o-tolyl)borate, dioctadecylmethylammonium tetrakis(pentafluorophenyl)borate, dioctadecylmethylammonium tetrakis(2,4-dimethylphenyl)borate, dioctadecylmethylammonium tetrakis(3,5-dimethylphenyl)borate, dioctadecylmethylammonium tetrakis(4-trifluoromethylphenyl)borate, dioctadecylmethylammonium tetrakis(3,5-ditrifluoromethylphenyl)borate, and dioctadecylmethylammonium.

Examples of the N,N-dialkylanilinium salt include N,N-dimethylanilinium tetraphenylborate, N,N-dimethylanilinium tetrakis(pentafluorophenyl)borate, N,N-dimethylanilinium tetrakis(3,5-ditrifluoromethylphenyl)borate, N,N-diethylanilinium tetraphenylborate, N,N-diethylanilinium tetrakis(pentafluorophenyl)borate, N,N-diethylanilinium tetrakis(3,5-ditrifluoromethylphenyl)borate, N,N-2,4,6-pentamethylanilinium tetraphenylborate, and N,N-2,4,6-pentamethylanilinium tetrakis(pentafluorophenyl)borate.

Examples of the dialkylammonium salt include di(1-propyl)ammonium tetrakis(pentafluorophenyl)borate, and dicyclohexylammonium tetrafluoroborate.

Further examples include ferrocenium tetrakis(pentafluorophenyl)borate, triphenylcarbenium pentaphenylcyclopentadienyl complex, N,N-diethylanilinium pentaphenylcyclopentadienyl complex, borate compounds represented by the following formula (3) or (4), borate compounds containing active hydrogen represented by the following formula (5), and borate compounds containing a silyl group represented by the following formula (6).

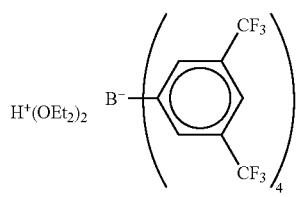

(In the formula, Et represents an ethyl group.)

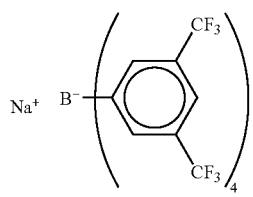

$$[B-Q_n(G_q(T-H)_r)_z]^- A^+ \quad (5)$$

In the formula (5), B represents boron. G represents a multi-binding hydrocarbon radical, examples of a preferable multi-binding hydrocarbon include alkylene having 1 to 20 carbon atoms, allylene, ethylene, and alkalylene radicals, and preferable examples of G include phenylene, bisphenylene, naphthalene, methylene, ethylene, propylene, 1,4-butadiene, and p-phenylenemethylene. The multi-binding radical G has r+1 bonds, that is, one bond binds to the borate anion, and other r bonds of G bind to the (T-H) groups. $A^+$ is a cation.

T in the above formula (5) represents O, S, $NR^j$, or $PR^j$, $R^j$ represents a hydrocarbanyl radical, a trihydrocarbanylsilyl radical, a trihydrocarbanylgermanium radical, or hydride, and q is an integer of 1 or larger, preferably 1. Examples of the T-H group include —OH, —SH, —$NR^jH$, and —$PR^jH$, wherein $R^j$ is a hydrocarbinyl radical having 1 to 18 carbon atoms, preferably 1 to 10 carbon atoms, or hydrogen. Examples of preferable $R^j$ group include alkyl, cycloalkyl, allyl, and allylalkyl, and alkylallyl groups having 1 to 18 carbon atoms. —OH, —SH, —$NR^jH$ or —$PR^jH$ may be, for example, —C(O)—OH, —C(S)—SH, —C(O)—$NR^jH$, or C(O)—$PR^jH$. The most preferable group having active hydrogen is —OH group. Q can be hydride, or a dihydrocarbylamide, preferably a dialkylamide, a halide, a hydrocarbyl oxide, an alkoxide, an allyloxide, a hydrocarbyl, or a substituted hydrocarbyl radical. In the formula, n+z is 4.

Examples of $[B-Q_n(G_q(T-H)_r)_z]$ of the above formula (5) include triphenyl(hydroxyphenyl)borate, diphenyl-di(hydroxyphenyl)borate, triphenyl(2,4-dihydroxyphenyl)borate, tri(p-tolyl)(hydroxyphenyl)borate, tris(pentafluorophenyl)(hydroxyphenyl)borate, tris(2,4-dimethylphenyl)(hydroxyphenyl)borate, tris(3,5-dimethylphenyl)(hydroxyphenyl)borate, tris[3,5-di(trifluoromehyl)phenyl](hydroxyphenyl)borate, tris(pentafluorophenyl)(2-hydroxyethyl)borate, tris(pentafluorophenyL)(4-hydroxybutyl)borate, tris(pentafluorophenyl)(4-hydroxycyclohexyl)borate, tris(pentafluorophenyl)[4-(4-hydroxyphenyl)phenyl]borate, and tris(pentafluorophenyl)(6-hydroxy-2-naphthyl)borate. The most preferable example is tris(pentafluorophenyl)(4-hydroxyphenyl)borate. Furthermore, compounds obtained by substituting the OH groups of the aforementioned borate compounds with —$NHR^j$ (wherein, $R^j$ is methyl, ethyl, or t-butyl) are also preferable.

Examples of $A^+$, which is a countercation of the borate compound, include a carbonium cation, a tropylium cation, an ammonium cation, an oxonium cation, a sulfonium cation, and a phosphonium cation. Further examples include positive ions of metals and positive ions of organometallics, which can easily be reduced. Examples of these cations include a triphenylcarbonium ion, a diphenylcarbonium ion, a cycloheptatrinium, indenium, triethylammonium, tripropylammonium, tributylammonium, dimethylammonium, dipropylammonium, dicyclohexylammonium, trioctylammonium, N,N-dimethylammonium, diethylammonium, 2,4,6-pentamethylammonium, N,N-dimethylphenylammonium, di-(i-propyl)ammonium, dicyclohexylammonium, triphenylphosphonium, triphosphonium, tridimethylphenylphosphonium, tri(methylphenyl)phosphonium, a triphenylphosphonium ion, a triphenyloxonium ion, a triethyloxonium ion, pyrinium, a silver ion, a gold ion, a platinum ion, a copper ion, a palladium ion, a mercury ion, and a ferrocenium ion. Inter alia, an ammonium ion is preferable.

$$[B-Q_n(G_q(S_iR^kR^lR^m)_r)_z]^- A^+ \quad (6)$$

In the formula (6), B represents boron. G represents a multi-binding hydrocarbon radical. Preferable examples of the multi-binding hydrocarbon include alkylene, allylene, ethylene, and alkalylene radicals having 1 to 20 carbon atoms, and preferable examples of G include phenylene, bisphenylene, naphthalene, methylene, ethylene, propylene, 1,4-butadiene, and p-phenylenemethylene. The multi-binding radical G has r+1 bonds, that is, one bond binds to the borate anion, and other r bonds bind to the ($SiR^kR^lR^m$) groups. $A^+$ is a cation.

Each of $R^k$, $R^l$ and $R^m$ in the above formula independently represents a hydrocarbanyl radical, a trihydrocarbanylsilyl radical, a trihydrocarbanylgermanium radical, hydrogen radical, an alkoxy radical, a hydroxyl radical or a halogen compound radical. $R^k$, $R^l$ and $R^m$ may be the same or independent. Q can be a hydride, or a dihydrocarbylamide, preferably a dialkylamide, a halide, a hydrocarbyl oxide, an alkoxide, an allyl oxide, a hydrocarbyl, or substituted hydrocarbyl radical, more preferably pentafluorobenzyl radical. In the formula, n+z is 4.

Examples of $[B-Q_n(G_q(S_rR^kR^lR^m)_r)_z]^-$ in the above formula (6) include triphenyl(4-dimethylchlorosilylphenyl)borate, diphenyl-di(4-dimethylchlorosilylphenyl)borate, triphenyl(4-dimethylmethoxysilylphenyl)borate, tri(p-tolyl)(4-triethoxysilylphenyl)borate, tris(pentafluorophenyl)(4-dimethylchlorosilylphenyl)borate, tris(pentafluorophenyl)(4-dimethylmethoxysilylphenyl)borate, tris(pentafluorophenyl)(4-trimethoxysilylphenyl)borate, and tris(pentafluorophenyl)(6-dimethylchlorosilyl-2-naphthyl)bo rate.

Examples of $A^+$, which is a countercation of the borate compound, include the same $A^+$'s as those in the above formula (5).

Examples of the borane compound include salts of anions such as decaborane, bis[tri(n-butyl)ammonium]nonaborate, bis[tri(n-butyl)ammonium]decaborate, bis[tri(n-butyl)ammonium]undecaborate, bis[tri(n-butyl)ammonium]dodecaborate, bis[tri(n-butyl)ammonium]decachlorodecaborate, and bis[tri(butyl)ammonium]dodecachlorododecaborate; and salts of metal boran anions such as tri(n-butyl)ammonium bis(dodecahydridedodecaborate)cobaltate (III), and bis[tri(n-butyl)ammonium] bis(dodecahydridedodecaborate)nickelate (III).

Examples of the carborane compound include salts of anions such as 4-carbanonaborane, 1,3-dicarbanonaborane, 6,9-dicarbadecaborane, dodecahydride-1-phenyl-1,3-dicarbanonaborane, dodecahydride-1-methyl-1,3-dicarbanonaboarne, undecahydride-1,3-dimethyl-1,3-dicarbanonaborane, 7,8-dicarbaundecaborane, 2,7-dicarbaundecaborane, undecahydride-7,8-dimethyl-7,8-dicarbaundecaborane, dodecahydride-11-methyl-2,7-dicarbaundecaborane, tri(n-butyl)ammonium 1-carbadecaborate, tri(n-butyl)ammonium 1-carbaundecaborate, tri(n-butyl)ammonium 1-carbadodecaborate, tri(n-butyl)ammonium 1-trimethylsilyl-1-carbadecaborate, tri(n-butyl)ammonium bromo-1-carbadodecaborate, tri(n-butyl)ammonium 6-carbadecaborate, tri(n-butyl)ammonium 6-carbadecaborate, tri(n-butyl)ammonium 7-carbaundecaborate, tri(n-butyl)ammonium 7,8-dicarbaundecaborate, tri(n-butyl)ammonium 2,9-dicarbaundecaborate, tri(n-butyl)ammonium dodecahydride-8-methyl-7,9-dicarbaundecaborate, tri(n-butyl)ammonium undecahydride-8-ethyl-7,9-dicarbaundecaborate, tri(n-butyl)ammonium undecahydride-8-butyl-7,9-dicarbaundecaborate, tri(n-butyl)ammonium undecahydride-8-allyl-7,9-dicarbaundecaborate, tri(n-butyl)ammonium undecahydride-9-trimethylsilyl-7,8-dicarbaundecaborate, and tri(n-butyl)ammonium undecahydride-4,6-bromo-7-carbaundecaborate; and salts of metal carborane anions such as tri(n-butyl)ammonium bis(nonahydride-1,3-dicarbanonaborate)cobaltate(III), tri(n-butyl)ammonium bis(undecahydride-7,8-dicarbaundecaborate)ferrate(III), tri(n-butyl)ammonium bis(undecahydride-7,8-dicarbaundecaborate)cobaltate(III), tri(n-butyl) ammonium bis(undecahydride-7,8-dicarbaundecaborate) nickelate(III), tri(n-butyl)ammonium bis(undecahydride-7,8-dicarbaundecaborate)cuprate(III), tri(n-butyl)ammonium bis(undecahydride-7,8-dicarbaundecaborate)aurate(III), tri(n-butyl)ammonium bis(nonahydride-7,8-dimethyl-7,8-dicarbaundecaborate)ferrate (III), tri(n-butyl)ammonium bis(nonahydride-7,8-dimethyl-7,8-dicarbaundecaborate) chromate(III), tri(n-butyl)ammonium bis(tribromooctahydride-7,8-dicarbaundecaborate)cobaltate (III), tris[tri(n-butyl)ammonium] bis(undecahydride-7-carbaundecaborate)chromate(III), bis[tri(n-butyl)ammonium] bis(undecahydride-7-carbaundecaborate)manganate(IV), bis[tri(n-butyl)ammonium]bis(undecahydride-7-carbaundecaborate)cobaltate(III), and bis[tri(n-butyl)ammonium]bis (undecahydride-7-carbaundecaborate)nickelate(IV).

Two or more kinds of compounds (B-4) which react with the aforementioned Group 4 transition metal compound (A) to form an ion pair may be used by mixing them.

In preparation of an olefin polymerization catalyst of the present invention, a carrier can be used if necessary. The carrier is usually an inorganic or organic compound, and is granular or fine particle solid. Among them, examples of the inorganic compound include porous oxides, inorganic chlorides, clays, clay minerals and ion-exchanging layer compounds.

As the porous oxide, specifically, $SiO_2$, $Al_2O_3$, MgO, ZrO, $TiO_2$, $B_2O_3$, CaO, ZnO, BaO, or $ThO_2$, or a compound oxide or a mixture containing them, for example, natural or synthetic zeolite, $SiO_2$—MgO, $SiO_2$—$Al_2O_3$, $SiO_2$—$TiO_2$, $SiO_2$—$V_2O_5$, $SiO_2$—$Cr_2O_3$, and $SiO_2$—$TiO_2$—MgO can be used.

In the present invention, an olefin low molecular weight polymer is prepared by polymerizing an olefin alone, or copolymerizing olefins in the presence of the aforementioned olefin polymerization catalyst.

Herein, examples of the olefin include olefins having 2 to 20 carbon atoms, preferably 2 to 16 carbon atoms, such as ethylene, propylene, 1-butene, 1-pentene, 1-hexene, 4-methyl-1-pentene, 3-methyl-1-pentene, 1-octene, 1-nonene, 1-decene, 1-undecene, 1-dodecene, 1-tetradecene, 1-hexadecene, 1-octadecene, and 1-eicocene. These olefins having 2 to 20 carbon atoms may be used by arbitrarily combining two or more species.

It is preferable that at least one of olefins to be polymerized is ethylene, propylene, 1-octene, 1-decene, 1-dodecene or 1-tetradecene. Particularly preferable are homopolymerization of ethylene, copolymerization of ethylene and other olefin, homopolymerization of propylene, homopolymerization of 1-octene, homopolymerizaiton of 1-decene, homopolymerization of 1-dodecene and homopolymerization of 1-tetradecene.

Specific modes for preparing the olefin low molecular weight polymer of the present invention will be explained in detail below.

In the present invention, a polymerization reaction is performed in a hydrocarbon medium. Examples of such the hydrocarbon medium include aliphatic hydrocarbons such as propane, butane, pentane, hexane, heptane, octane, decane and dodecane; alicyclic hydrocarbons such as cyclopentane, cyclohexane, and methylcyclopentane; aromatic hydrocarbons such as benzene, toluene, and xylene; halogenated hydrocarbons such as ethylene chloride, chlorobenzene, and dichloromethane; and petroleum fractions such as gasoline, kerosene, and gas oil. Furthermore, the olefins used for polymerization may be used.

In the present invention, polymerization is performed in the presence of such an olefin polymerization catalyst. In this case, the Group 4 transition metal compound (A) is used in an amount in a range of usually from $10^{-8}$ to $10^{-2}$ gram atom/liter, preferably from $10^{-7}$ to $10^{-3}$ gram atom/liter in terms of the concentration of the transition metal atom in the polymerizing reaction system.

The component (B-1) is used in such an amount that the molar ratio of the component (B-1) to the total transition metal atom (M) in the component (A) [(B-1)/M] is usually in the range of from 0.01 to 5,000, preferably from 0.05 to 2,000. The component (B-2) is used in such an amount that the molar ratio of the component (B-2) to the total transition metal atom (M) in the component (A) [(B-2)/M] is usually in the range of from 100 to 25,000, preferably from 500 to 10,000. The component (B-3) is used in such an amount that the molar ratio of the aluminum atom in the component (B-3) and the total transition metal (M) in the component (A) [(B-3)/M] is usually in the range of from 10 to 5,000, preferably from 20 to 2,000. The component (B-4) is used in such an amount that the molar ratio of the component (B-4) to the transition metal atom (M) in the component (A) [(B-4)/M] is usually in the range of from 1 to 50, preferably 1 to 20.

When olefins are copolymerized in an arbitrary combination, the composition of the olefins as raw materials can be appropriately selected, depending the type of the low molecular weight olefin (co)polymer to be obtained. For example, in copolymerization using ethylene as a main monomer, it is preferable that the content of ethylene in raw material olefins is in the range of usually from 60 to 100 mol %, preferably from 70 to 100 mol %, and the content of the other olefin(s) is in the range of usually from 0 to 40 mol %, preferably from 0 to 30 mol %.

In the present invention, it is preferable that polymerization is performed at a temperature in the range of from 50 to 250° C. When ethylene is used as a main monomer, it is desirable that polymerization is performed at a temperature in the range of preferably from 100 to 250° C., more preferably from 120 to 250° C., particularly preferably from 130 to 200° C.

When a polymerization temperature is in the aforementioned range, it is easy to remove the heat in the polymerization system, and a heat removal device can be miniaturized. In addition, even with the same heat removal device, since the heat removing efficacy is enhanced, the productivity can be improved. Furthermore, since polymerization is performed at a high temperature, even when the polymer concentration is increased, the solution viscosity is not increased so much, thus the stirring power required can be reduced, and the polymerization can be performed at high concentration, thereby improving the productivity.

Usually, when an olefin is (co)polymerized, the heat is removed by circulating a solvent in order to stabilize the polymerizing temperature. In a heat removal device usually used herein, when an amount of heat to be removed is the same, as a polymerization temperature grows higher, a heat transfer area can generally be made smaller. The effect thereof varies depending on the conditions such as a cooling medium and so on. For example, when a simple counter-current-type heat exchanger employing cooling water is used, in the case where a polymerizing temperature is 100° C., a necessary heat transfer area can be reduced to about ½ of that required in a polymerization at a temperature of 70° C. As described above, when a polymerization temperature is raised, the heat transfer area required can be made smaller, and a heat removal device can be miniaturized, thus, equipment cost can be reduced.

It is preferable that the average residence time (polymerizing time) is 2 hours or shorter, preferably 1 hour or shorter. The polymerizing pressure is usually in a range of from atmospheric pressure to 100 kg/cm², preferably from atmospheric pressure to 50 kg/cm², more preferably from atmospheric pressure to 40 kg/cm².

The molecular weight of the resulting low molecular weight olefin (co)polymer can be controlled by an amount of hydrogen supplied to the polymerization reaction system and/or the polymerizing temperature. The amount of hydrogen to be supplied to the polymerization reaction system is in the range of usually from 0.01 to 2, preferably from 0.05 to 1, in terms of the molar ratio of hydrogen to the olefin.

In the present invention, a low molecular weight olefin (co)polymer is obtained by treating the polymerization products mixture after completion of the polymerization reaction according to the conventional method.

A molecular weight distribution (Mw/Mn) of the low molecular weight olefin (co)polymer of the present invention measured by gel permeation chromatography (GPC) is usually 3 or smaller, preferably 2.5 or smaller.

An intrinsic viscosity [η] of the low molecular weight olefin (co)polymer of the present invention measured at 135° C. in decalin is in the range of 0.60 dl/g or smaller, preferably 0.40 dl/g or smaller, more preferably from 0.005 to 0.40 dl/g, further preferably from 0.005 to 0.35 dl/g, particularly preferably from 0.01 to 0.30 dl/g. Among the polymers above, a low molecular weight olefin (co)polymer using ethylene as a main monomer is usually called ethylene wax. It is preferable that the content of an ethylene component unit therein is in the range of from 80 to 100 mol %, preferably from 85 to 100 mol %. It is preferable that the content of an olefin component unit having 3 or more carbon atoms is in the range of from 0 to 20 mol %, preferably from 0 to 15 mol %. A melting point of the ethylene wax obtained in the present invention is usually 132° C. or lower.

According to the present invention, a low molecular weight olefin (co)polymer can be prepared with high productivity. In addition, when a polymerizing temperature is 100° C. or higher, a low molecular weight olefin (co) polymer having a narrow molecular weight distribution and a low melting point can be prepared with high productivity. Furthermore, a heat removal device can be miniaturized, the equipment cost can be reduced and, at the same time, the residence time can be shortened.

The novel Group 4 transition metal compound represented by the aforementioned general formula (1') can be prepared, for example, by the process described in J. Organomet. Chem., 361, 37 (1998). A specific process will be shown below, without limiting the scope of the invention in any way.

For example, the compound of the general formula (1') can be prepared by the following steps.

First, a precursor compound [20] of the general formula (1') can be prepared by the method of the following process [A] or [B].

Process [A]:

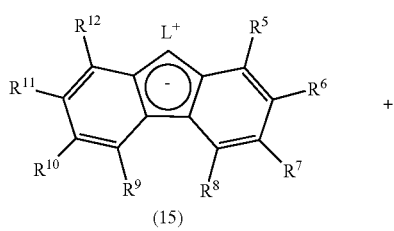

(15)

-continued

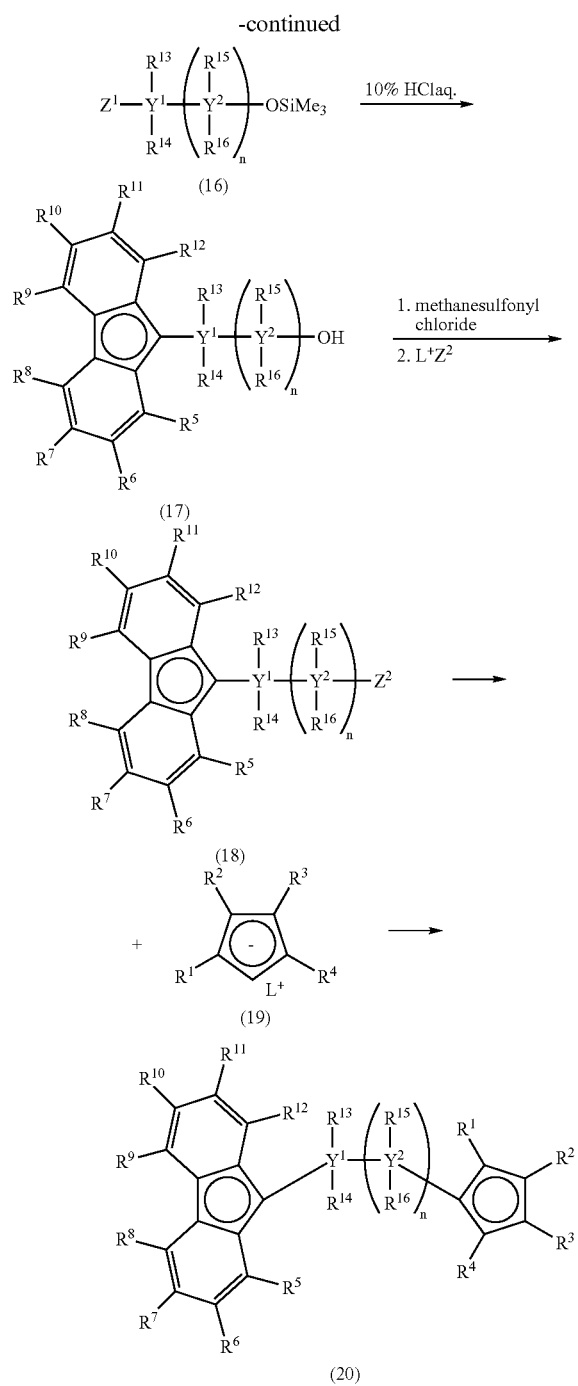

Process [B]:

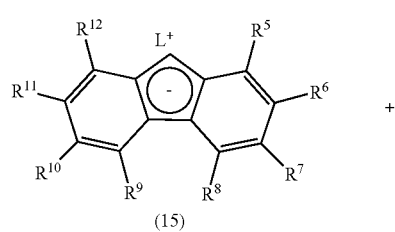

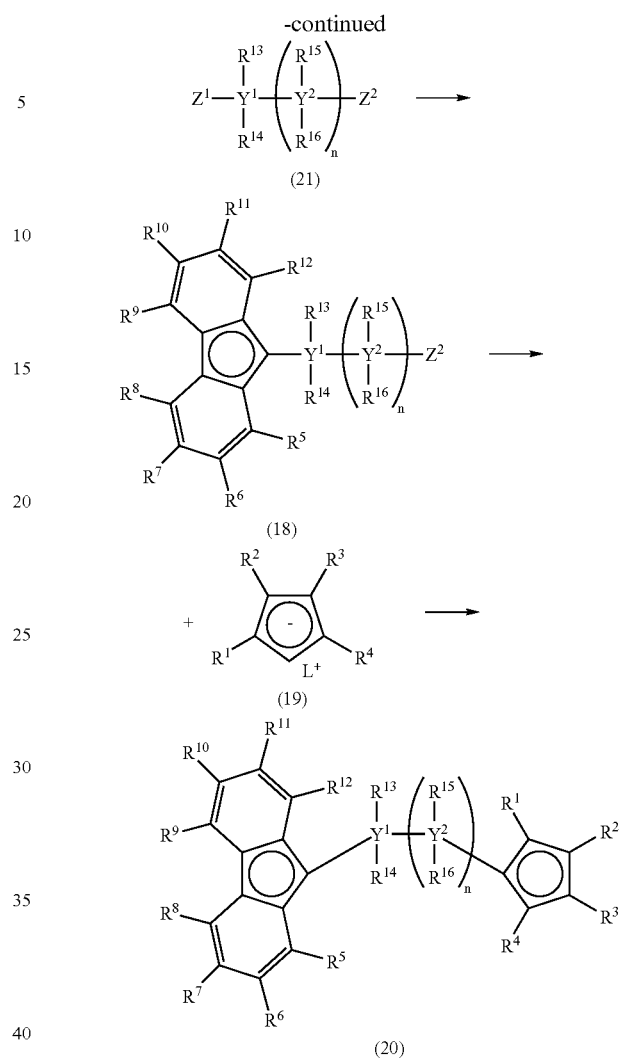

(In the formula, $R^1$ to $R^{16}$, and Y are same as defined in the general formula (1'), L is an alkali metal, and each of $Z^1$ and $Z^2$ is a halogen or an anionic ligand, and may be the same or different from each other.)

Further, a precursor of a cyclopentadienyl ligand of the formula (1'), for example, (24) wherein each of $R^2$ and $R^4$ is a hydrogen atom in the precursor, can be prepared selectively by the following Process [C].

Process [C]:

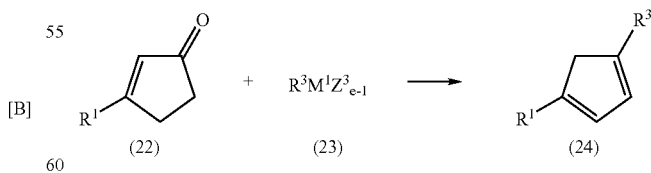

(In the formula, $R^1$ and $R^3$ are same as defined in the general formula (1'), $M^1$ is an alkali metal or an alkaline earth metal, $Z^3$ is the same as $R^3$, or a halogen or an anionic ligand, and e is a valence number of $M^1$.)

In addition, as a substitute process for producing (24), there are the following Process [D] and Process [E]. In these processes, an isomer, wherein $R^1$ and $R^3$ are adjacent to each other in (24), is produced as a side product in some cases. Therefore, the Process [D] and the Process [E] can be employed, depending on a combination of $R^1$ and $R^3$ and the reaction conditions, as far as the isomer is not produced as a side product.

Process [D]:

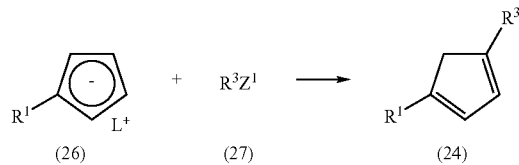

Process [E]:

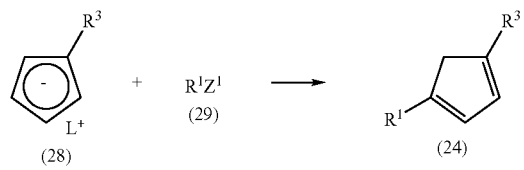

(In the formula, $R^1$ and $R^3$ are same as defined in the general formula (1'), L is an alkali metal, and $Z^1$ is a halogen or an anionic ligand.)

Furthermore, when $R^3$ is a substituent represented by $CR^{17}R^{18}R^{19}$, (24) may also be prepared by the following Process [F].

Process [F]:

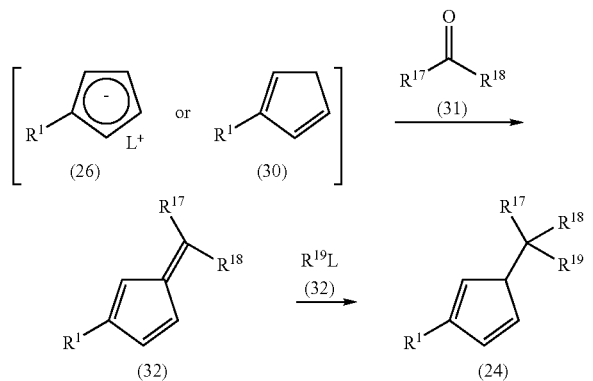

(In the formula, $R^1$ is as defined in the general formula (1'), each of $R^{17}$, $R^{18}$ and $R^{19}$ is independently selected from hydrogen, a hydrocarbon group and a silicon-containing hydrocarbon group, and may be the same or different from each other, and L is an alkali metal.)

Also in this process, since an isomer of (24) wherein $R^1$ and $R^3$ are adjacent to each other is produced as a side product in some cases, the Process [F] can be employed, depending on a combination of $R^1$ and $R^3$ and the reaction conditions, as far as the isomer is not produced as a side product.

Examples of the alkali metal used in the reactions of the above Processes [A] to [F] include lithium, sodium and potassium and examples of the alkaline earth metal include magnesium and calcium. In addition, examples of the halogen include fluorine, chlorine, bromine and iodine. Examples of the anionic ligand include alkoxy groups such as methoxy, tert-butoxy and phenoxy; carboxylate groups such as acetate and benzoate; sulfonate groups such as mesylate and tosylate; and so on.

Next, an example of preparing a metallocene compound from the precursor compounds of the general formula (20) will be shown. However, this does not limit the scope of the invention, and the metallocene compound may be prepared by appropriately selecting other processes.

The precursor compound of the general formula (20) obtained by the reaction of the Process [A] or [B] is contacted with an alkali metal, an alkali metal hydride or an organic alkali metal at a reaction temperature in the range of from –80 to 200° C. in an organic solvent to obtain a dialkali metal salt.

Examples of the organic solvent used in the above reaction include aliphatic hydrocarbons such as pentane, hexane, heptane, cyclohexane and decalin; aromatic hydrocarbons such as benzene, toluene and xylene; ethers such as THF, diethyl ether, dioxane and 1,2-dimethoxyethane; halogenated hydrocarbons such as dichloromethane and chloroform; and so on.

Example of the alkali metal used in the above reaction include lithium, sodium, potassium and so on, examples of the alkali metal hydride include sodium hydride, potassium hydride and so on, and examples of the organic alkali metal include methyllithium, butyllithium, phenyllithium and so on.

Then, a metallocene compound represented by the general formula (1') can be synthesized by reacting the aforementioned dialkali metal salt with a compound represented by the following general formula (33) in an organic solvent.

$$MZ_k \qquad (33)$$

(In the formula, M is a metal selected from Group 4 of the Periodic Table, each Z may be independently selected from a halogen, an anionic ligand and a neutral ligand which can be coordinated with a lone electron pair, and k is an integer of 3 to 6.)

Preferable examples of the compound represented by the general formula (33) include trivalent or tetravalent titanium fluoride, chloride, bromide and iodide; tetravalent zirconium fluoride, chloride, bromide and iodide; tetravalent hafnium fluoride, chloride, bromide and iodide; and complexes of these compounds and ethers such as THF, diethyl ether, dioxane and 1,2-dimethoxyethane.

In addition, examples of the organic solvent to be used include those as described above. A reaction of the dialkali metal salt and the compound represented by the general formula (33) is preferably performed by an equimolar reaction, and can be performed at a reaction temperature in a range of from –80 to 200° C. in the aforementioned organic solvent.

The metallocene compound obtained in the reaction can be isolated and purified by a method such as extraction, recrystallization or sublimation. In addition, the bridged metallocene compound of the present invention obtained by such a process can be identified by using an analyzing procedure such as proton nuclear magnetic resonance spectrum, $^{13}C$ nuclear magnetic resonance spectrum, mass spectrometry or elementary analysis.

Since the low molecular weight olefin (co)polymer obtained by the present invention, in particular, the low-molecular weight ethylene (co)polymer has a narrow molecular weight distribution and a low melting point, the polymer can be suitably used in utilities such as a paint modifier, a glazing agent, a pigment dispersant (in particular, a raw material for pigment master batch), a lubricant for polyvinyl chloride, a resin molding lubricant, a rubber processing aid, a releasing agent for toner, a paper improver, an ink anti-abrasion agent, a fiber processing aid, a hot melt adhesive additive, an electrical insulator, a natural wax component, an asphalt flowability improver, various oil hardeners, a communication cable filler, a raw material for moisture proof coating agent, a peel ability imparting agent for paper coating, a polymer emulsifying aid for suspension or emulsion polymerization, a base material for antistatic or weathering agent, an automobile engine oil, a gear oil, ATF, a base oil and a viscosity index improver for the industrial lubricant, a base oil for grease, a metal processing oil, a rubber/resin modifier, a releasing agent for aluminum die casting, a fuel oil additive, a paint, and an ink modifier.

EXAMPLES

The present invention will be more specifically explained below by way of Examples, but the present invention is not limited by these Examples.

The physical properties and the characteristics of the resulting polymers were measured by the following methods.

[Weight Average Molecular Weight (Mw), Number Average Molecular Weight (Mn)]

These molecular weights were measured using GPC-150C (manufactured by Waters Corporation) as follows: separation columns used were TSKgel GMH6-HT and TSKgel GMH6-HTL, the column had a size of 7.5 mm in inner diameter and 600 mm in length, the column temperature was 140° C., the mobile phase was o-dichlorobenzene (Wako Pure Chemical Industries, Ltd.) and 0.025 wt. % of BHT (Takeda Chemical Industries, Ltd.) as an antioxidant, the mobile phase was moved at 1.0 ml/min, the sample concentration was 0.1 wt. %, the sample injection amount was 500 μl, and the detector used was a differential refractometer. As a standard polystyrene, a polystyrene manufactured by Tosoh Corporation was used for a molecular weight range of Mw<1,000 and Mw>4×10$^6$, and a polystyrene manufactured by Pressure Chemical Co, was used for a molecular weight range of 1,000≦Mw≦4×10$^6$.

[Intrinsic Viscosity ([η])]

The intrinsic viscosity was measured at 135° C. using a decalin solvent. About 20 mg of a granulated pellet was dissolved in 15 ml of decalin, and a specific viscosity $\eta_{sp}$ is measured in an oil bath at 135° C. Five ml of a decalin solvent is added to this decalin solution to dilute the solution, and a specific viscosity $\eta_{sp}$ is measured similarly. This diluting procedure is further repeated two times, and a $\eta_{sp}/C$ value when the concentration (C) is extrapolated to 0 is calculated and obtained as an intrinsic viscosity.

$$[\eta]=\lim(\eta_{sp}/C)(C\to 0)$$

[Melt Flow Rate (MFR$_{10}$)]

This is a numerical value measured at 190° C. under 10 kg load by a standard method of ASTM D-1238.

[Density]

A strand after the measurement of MFR at 190° C. under 2.16 kg load was heat-treated at 120° C. for 1 hour, and gradually cooled to room temperature over 1 hour and, thereafter, the density was measured by a density gradient tube method.

[Melting Point (Tm)]

By differential scanning calorimetry (DSC), a polymer sample was held at 240° C. for 10 minutes, cooled to 30° C., held for 5 minutes, and, thereafter, a temperature of the sample was raised at 10° C./min. The melting point was calculated from a crystal melting peak measured during the temperature raise.

Example 1

One liter of hexane was charged into an stainless autoclave having an inner volume of 2 liter which had been sufficiently replaced with nitrogen, the temperature in the system was raised to 145° C., and hydrogen was introduced to make a total pressure in the system reach 0.3 MPa-G. Thereafter, the total pressure was retained at 3 MPa-G by continuously supplying only ethylene. Then, 0.3 mmol of triisobutylaluminum, 0.04 mmol of N,N-dimethylanilinium tetrakis(pentafluorophenyl)borate and 0.00005 mmol of ethylene(1-cyclopentadienyl)(fluorenyl)zirconium dichloride were charged therein with nitrogen to initiate polymerization. The polymerization was performed at 150° C. for 30 minutes. The polymerization was stopped by addition of a small amount of ethanol to the system, and unreacted ethylene was purged. The resulting polymer solution was dried at 80° C. overnight under reduced pressure. As a result, 20.0 g of an ethylene polymer having [η] of 0.05 dl/g was obtained. The results are shown in Table 1.

Example 2

One liter of hexane was charged into a stainless autoclave having an inner volume of 2 liter which had been sufficiently replaced with nitrogen, the temperature in the system was raised to 145° C., and hydrogen was introduced to make a total pressure in the system reach 0.2 MPa-G. Thereafter, the total pressure was retained at 3 MPa-G by continuously supplying only ethylene. Then, 0.3 mmol of triisobutylaluminum, 0.04 mmol of N, N-dimethylanilinium tetrakis(pentafluorophenyl)borate and 0.00005 mmol of ethylene(1-cyclopentadienyl)(fluorenyl)zirconium dichloride were charged therein with nitrogen to initiate polymerization. The polymerization was performed at 150° C. for 30 minutes. The polymerization was stopped by addition of a small amount of ethanol to the system, and unreacted ethylene was purged. The resulting polymer solution was dried at 80° C. overnight under reduced pressure. As a result, 32.0 g of an ethylene polymer having [η] of 0.11 dl/g was obtained. The results are shown in Table 1.

Example 3

One liter of hexane was charged into a stainless autoclave having an inner volume of 2 liter which had been sufficiently replaced with nitrogen, the temperature in the system was raised to 145° C., and hydrogen was introduced to make a total pressure in the system reach 1.0 MPa-G. Thereafter, the total pressure was retained at 3 MPa-G by continuously supplying only ethylene. Then, 0.3 mmol of triisobutylaluminum, 0.04 mmol of N,N-dimethylanilinium tetrakis(pentafluorophenyl)borate and 0.0001 mmol of ethylene (1-cyclopentadienyl)(3,6-t-butylfluorenyl)zirconium dichloride were charged therein with nitrogen to initiate polymerization. The polymerization was performed at 150° C. for 30 minutes. The polymerization was stopped by addition of a small amount of ethanol to the system, and unreacted ethylene was purged. The resulting polymer solution was dried at 80° C. overnight under reduced pressure. As a result, 11.0 g of an ethylene polymer having [η] of 0.04 dl/g was obtained. The results are shown in Table 1.

Example 4

One liter of hexane was charged into a stainless autoclave having an inner volume of 2 liter which had been sufficiently replaced with nitrogen, the temperature in the system was raised to 145° C., and hydrogen was introduced to make a total pressure in the system reach 0.2 MPa-G. Thereafter, the total pressure was retained at 3 MPa-G by continuously supplying only ethylene. Then, 0.3 mmol of triisobutylaluminum, 0.04 mmol of N,N-dimethylanilinium tetrakis(pentafluorophenyl)borate and 0.00005 mmol of ethylene(1-cyclopentadienyl)(3,6-t-butylfluorenyl)zirconium dichloride were charged therein with nitrogen to initiate polymerization. The polymerization was performed at 150° C. for 30 minutes. The polymerization was stopped by addition of a small amount of ethanol to the system, and unreacted ethylene was purged.

Resulting polymer solution was dried at 80° C. overnight under reduced pressure. As a result, 16.1 g of an ethylene polymer having [η] of 0.22 dl/g was obtained. The results are shown in Table 1.

Comparative Example 1

One liter of hexane was charged into a stainless autoclave having an inner volume of 2 liter which had been sufficiently replaced with nitrogen, the temperature in the system was raised to 145° C., and hydrogen was introduced to make a total pressure in the system reach 1.3 MPa-G. Thereafter, the total pressure was retained at 3 MPa-G by continuously supplying only ethylene. Then, 0.3 mmol of triisobutylaluminum, 0.04 mmol of N,N-dimethylanilinium tetrakis(pentafluorophenyl)borate and 0.0002 mmol of ethylene bis(indenyl)zirconium dichloride were charged therein with nitrogen to initiate polymerization. The polymerization was performed at 150° C. for 30 minutes. The polymerization was stopped by addition of a small amount of ethanol to the system, and unreacted ethylene was purged. The resulting polymer solution was dried at 80° C. overnight under reduced pressure. As a result, 12.7 g of an ethylene polymer having [η] of 0.04 dl/g was obtained. The results are shown in Table 1.

Example 5

One liter of hexane was charged into a stainless autoclave having an inner volume of 2 liter which had been sufficiently replaced with nitrogen and, subsequently, 100 g of propylene was charged therein. The temperature in the system was raised to 145° C., the total pressure was retained at 3 MPa-G by continuously supplying only ethylene. Then, 0.3 mmol of triisobutylaluminum, 0.04 mmol of N,N-dimethylanilinium tetrakis(pentafluorophenyl)borate and 0.0002 mmol of ethylene(1-cyclopentadienyl)(fluorenyl)zirconium dichloride were charged therein with nitrogen to initiate polymerization. The polymerization was performed at 150° C. for 30 minutes. The polymerization was stopped by addition of a small amount of ethanol to the system, and unreacted ethylene was purged. The resulting polymer solution was dried at 80° C. overnight under reduced pressure. As a result, 23.6 g of an ethylene polymer having [η] of 0.56 dl/g was obtained. The results are shown in Table 2.

Example 6

One liter of hexane was charged into a stainless autoclave having an inner volume of 2 liter which had been sufficiently replaced with nitrogen and, subsequently, 80 g of propylene was charged therein. The temperature in the system was raised to 145° C., and hydrogen was introduced to make a total pressure in the system reach 0.1 MBa-G. Thereafter, the total pressure was retained at 3 MPa-G by continuously supplying only ethylene. Then, 0.3 mmol of triisobutylaluminum, 0.04 mmol of N,N-dimethylanilinium tetrakis(pentafluorophenyl)borate and 0.0002 mmol of ethylene(1-cyclopentadienyl)(fluorenyl)zirconium dichloride were charged therein with nitrogen to initiate polymerization. The polymerization was performed at 150° C. for 30 minutes. The polymerization was stopped by addition of a small amount of ethanol to the system, and unreacted ethylene was purged. The resulting polymer solution was dried at 80° C. overnight under reduced pressure. As a result, 28.8 g of an ethylene polymer having [η] of 0.18 dl/g was obtained. The results are shown in Table 2.

TABLE 1

| | Component (A) | | Component (B) | | | | Hydrogen Pressure *1 | Polymerization temperature (° C.) | Polymerization time (min) | Yield (g) | [η] (dl/g) | Polymerization activity *2 |
|---|---|---|---|---|---|---|---|---|---|---|---|---|
| | Kind | Amount (mmol) | Kind | Amount (mmol) | Kind | Amount (mmol) | | | | | | |
| Example 1 | a | 0.00005 | I | 0.04 | TIBA | 0.3 | 0.3 | 150 | 30 | 20 | 0.05 | 400,000 |
| Example 2 | a | 0.00005 | I | 0.04 | TIBA | 0.3 | 0.2 | 150 | 30 | 32 | 0.11 | 640,000 |
| Example 3 | b | 0.0001 | I | 0.04 | TIBA | 0.3 | 1.0 | 150 | 30 | 11 | 0.04 | 110,000 |
| Example 4 | b | 0.00005 | I | 0.04 | TIBA | 0.3 | 0.2 | 150 | 30 | 16.1 | 0.22 | 322,000 |
| Comparative Example 1 | c | 0.0002 | I | 0.04 | TIBA | 0.3 | 1.3 | 150 | 30 | 12.7 | 0.04 | 63,500 | a: Ethylene(1-cyclopentadienyl)(fluorenyl)zirconium dichloride
b: Ethylene(1-cyclopentadienyl)(3,6-tBu2fluorenyl)zirconium dichloride
c: Ethylenebis(indenyl)zirconium dichloride
I: N,N-dimethylanilinium tetrakis(pentafluorophenyl)borate
TIBA: Triisobutylaluminum
*1: Mpa-G
*2: g-PE/mmol-Zr

TABLE 2

| | (A) | | Component (B) | | | | Component Hydrogen pressure *1 | Polymerization temperature (° C.) | Polymerization time (min) | Yield (g) | [η] (dl/g) | Density (kg/m³) | Polymerization activity *2 |
|---|---|---|---|---|---|---|---|---|---|---|---|---|---|
| | Kind | Amount (mmol) | Kind | Amount (mmol) | Kind | Amount (mmol) | Propylene (g) | | | | | | |
| Example 5 | a | 0.0002 | I | 0.04 | TIBA | 0.3 | 100.0 | 0 | 150 | 30 | 23.6 | 0.56 | 902 | 118,000 |
| Example 6 | a | 0.0002 | I | 0.04 | TIBA | 0.3 | 80.0 | 0.1 | 150 | 30 | 28.8 | 0.18 | 897 | 144,000 | a: Ethylene(1-cyclopentadienyl)(fluorenyl)zirconium dichloride
I: N,N-dimethylanilinium tetrakis(pentafluorophenyl)borate
TIBA: Triisobutylaluminum
*1: Mpa-G
*2: g-Polymer/mmol-Zr Example 7

A glass autoclave having an inner volume of 1000 ml was equipped with a thermometer, a gas blowing tube and a glass stirring wing, and sufficiently replaced with nitrogen. Thereafter, 250 ml of n-decane and 250 ml of 1-decene were charged into the autoclave, and the temperature in the system was raised to 90° C. while nitrogen was being flown therein at an amount of 50 liter/hr. On the other hand, a magnetic stirrer chip was placed into a flask with a branch having an inner volume of 30 ml, which had been sufficiently replaced with nitrogen, and 0.002 mmol of a toluene solution of ethylene(1-cyclopentadienyl)(fluorenyl)zirconium dichloride as a transition metal compound, and 2 mmol of a toluene solution of methylaluminoxane (1.53M of Al) were added thereto, followed by stirring for 30 minutes. The nitrogen flow to the glass autoclave was stopped, then hydrogen was flown at an amount of 20 liter/hr, and the aforementioned solution was added to initiate polymerization. During the polymerization, hydrogen was continuously supplied at an amount of 20 liter/hr, the polymerization was performed at 90° C. for 60 minutes under normal pressure, and the polymerization was stopped by addition of a small amount of isopropanol. The obtained polymer solution was added in 300 ml of 1N hydrochloric acid, followed by stirring. This solution was transferred to a separating funnel, the organic layer was taken, the organic layer was washed with water, and the solvent and unreacted 1-decene were distilled off at 175° C. under reduced pressure (1 mmHg). The resulting transparent liquid polymer was 97.17 g, and the polymerization activity was 48.59 kg-polymer/mmol-Zr/hr. The polymer was analyzed. [η] was 0.04 dl/g, Mw was 4,250, Mn was 2,320, and Mw/Mn was 1.64. The results are shown in Table 3.

Example 8

The same procedures as those of Example 7 were performed except that the polymerization temperature was changed to 60° C., and the amount of hydrogen was changed to 10 liter/hr.
The weight of the resulting transparent liquid polymer was 74.64 g, and the polymerization activity was 37.32 kg-polymer/mmol-Zr/hr. The polymer was analyzed. [η] was 0.09 dl/g, Mw was 13,360, Mn was 7,220, and Mw/Mn was 1.85. The results are shown in Table 3.

Example 9

The same procedures as those of Example 7 were performed except that the polymerization temperature was changed to 70° C., and the amount of hydrogen was changed to 50 liter/hr.
The weight of the resulting transparent liquid polymer was 77.34 g, and the polymerization activity was 38.67 kg-polymer/mmol-Zr/hr. The polymer was analyzed. [η] was 0.06 dl/g, Mw was 9.720, Mn was 5,170, and Mw/Mn was 1.88. The results are shown in Table 3.

Example 10

A glass autoclave having an inner volume of 1000 ml was equipped with a thermometer, a gas blowing tube and a glass stirring wing, and sufficiently replaced with nitrogen. Thereafter, 250 ml of n-decane and 250 ml of 1-decene were charged into the autoclave, and the temperature of the system was brought to 60° C. while nitrogen was being flown therein at an amount of 50 liter/hr. The flow nitrogen into the glass autoclave was stopped, hydrogen was flown at an amount of 10 liter/hr. Thereafter, 2 mmol of an n-decane solution of triisobutylaluminum was added. Then, 0.002 mmol of a toluene solution of ethylene(1-cyclopentadienyl)(fluorenyl)zirconium dichloride as a transition metal compound was added and, finally, 0.04 mmol of a toluene solution of N,N-dimethylaluminium tetrakis(pentafluorophenyl)borate was added to initiate polymerization. During the polymerization, hydrogen was continuously supplied at an amount of 10 liter/hr, the polymerization was performed at 60° C. for 60 minutes under normal pressure, and the polymerization was stopped by addition of a small amount of isopropanol. The polymer solution was added in 300 ml of 1N hydrochloric acid, followed by stirring. This solution was transferred to a separating funnel, the organic layer was taken, thereafter, the organic layer was washed with water, and the solvent and unreacted 1-decene were distilled off at 175° C. under reduced pressure (1 mmHg). The weight of the resulting transparent liquid polymer was 106.20 g, and the polymerization activity was 53.10 kg-polymer/mmol-Zr/hr. The polymer was analyzed. [η] was 0.13 dl/g, Mw was 22,670, Mn was 13,700, and Mw/Mn was 1.65. The results are shown in Table 3.

Example 11

A glass autoclave having an inner volume of 1000 ml was equipped with a thermometer, a gas blowing tube and a glass stirring wing, and sufficiently replaced with nitrogen. Thereafter, 400 ml of n-decane and 100 ml of 1-decene were charged into the autoclave, and a temperature was brought to 60° C. while nitrogen was being flown therein at an amount of 50 liter/hr. On the other hand, a magnetic stirrer chip was placed into a flask with a branch having an inner volume of 30 ml which had been sufficiently replaced with nitrogen, and 0.002 mmol of a toluene solution of ethylene(1-cyclopentadienyl)(fluorenyl)zirconium dichloride as a transition metal compound, and 2 mmol of a toluene solution of methylaluminoxane (1.53M of Al) were added thereto, followed by stirring for 30 minutes. The nitrogen flow into the glass autoclave was stopped, ethylene was flown for 5 minutes at an amount of 50 liter/hr, hydrogen was flown at an amount of 10 liter/hr while maintaining a flow rate of ethylene, and the aforementioned solution was added to initiate polymerization. During the polymerization, ethylene and hydrogen were continuously supplied at an amount of 50 liter/hr and 10 liter/hr, respectively. The polymerization was performed at 60° C. for 60 minutes under normal pressure, and the polymerization was stopped by addition of a small amount of isopropanol. The polymer solution was added in 300 ml of 1N hydrochloric acid, followed by stirring. This solution was transferred to a separating funnel, the organic layer was taken, the organic layer was washed with water, and the solvent and unreacted 1-decene were distilled off at 175° C. under reduced pressure (1 mmH). The weight of the resulting transparent liquid polymer was 49.49 g, and the polymerization activity was 27.74 kg-polymer/mmol-Zr/hr. The polymer was analyzed. [η] was 0.16 dl/g, Mw was 27,060, Mn was 17,980, and Mw/Mn was 1.51. The results are shown in Table 3.

Example 12

The same procedures as those of Example 7 were performed except that 1-decene as a monomer was changed to 1-octene, the polymerization temperature was changed to 50° C., and the amount of hydrogen was changed to 10 liter/hr.

The weight of the resulting transparent liquid polymer was 49.95 g, and the polymerization activity was 24.98 kg-polymer/mmol-Zr/hr. The polymer was analyzed. [η] was 0.10 dl/g, Mw was 16,700, Mn was 9,380, and Mw/Mn was 1.63. The results are shown in Table 3.

Example 13

The same procedures as those of Example 7 were performed except that 1-decene as a monomer was changed to 1-dodecene, the polymerization temperature was changed to 50° C., and the amount of the hydrogen was changed to 10 liter/hr.

The weight of the resulting transparent liquid polymer was 29.59 kg, and the polymerization activity was 14.80 kg-polymer/mmol-Zr/hr. The polymer was analyzed. [η] was 0.10 dl/g, Mw was 18,360, Mn was 11,400, and Mw/Mn was 1.61. The results are shown in Table 3.

Example 14

The same procedures as those of Example 7 were performed except that 1-decene as a monomer was changed to 1-tetradecene, the polymerization temperature was changed to 50° C., and the amount of hydrogen was changed to 10 liter/hr.

The weight of the resulting transparent liquid polymer was 20.40 kg, and the polymerization activity was 10.20 kg-polymer/mmol-Zr/hr. The polymer was analyzed. [η] was 0.11 dl/g, Mw was 23,570, Mn was 14,460, and Mw/Mn was 1.63. The results are shown in Table 3.

Example 15

The same procedures as those of Example 7 were performed except that ethylene (1-cyclopentadienyl)(fluorenyl) zirconium dichloride was changed to ethylene(1-cyclopentadienyl)(2,7-di-tert-butyl-fluorenyl)zirconium dichloride, the polymerization temperature was changed to 60° C., and the amount of the hydrogen was changed to 10 liter/hr.

The weight of the resulting transparent liquid polymer was 28.25 kg, and the polymerization activity was 14.13 kg-polymer/mmol-Zr/hr. The polymer was analyzed. [η] was 0.08 dl/g, Mw was 12,120, Mn was 7,410, and Mw/Mn was 1.64. The results are shown in Table 3.

Example 16

The same procedures as those of Example 7 were performed except that ethylene (1-cyclopentadienyl)(fluorenyl) zirconium dichloride was changed to ethylene(1-cyclopentadienyl)(octamethyloctahydrodibenzofluorenyl)zirconium dichloride, the polymerization temperature was changed to 80° C., and the amount of the hydrogen was changed to 35 liter/hr.

The weight of the resulting transparent liquid polymer was 47.51 kg, and the polymerization activity was 23.76 kg-polymer/mmol-Zr/hr. The polymer was analyzed. [η] was 0.07 dl/g, Mw was 9,910, Mn was 5,860, and Mw/Mn was 1.69. The results are shown in Table 3.

Example 17

Te same procedures as those of Example 7 were performed except that ethylene (1-cyclopentadienyl)(fluorenyl) zirconium dichloride was changed to ethylene (1-cyclopentadienyl)(octamethyloctahydrodibenzofluorenyl)zirconium dichloride, 1-decene as a monomer was changed to 1-dodecene, the polymerization temperature was changed to 50° C., and the amount of hydrogen was changed to 35 liter/hr.

The weight of the resulting transparent liquid polymer was 45.30 kg, and the polymerization activity was 22.65 kg-polymer/mmol-Zr/hr. The polymer was analyzed. [η] was 0.07 dl/g, Mw was 8,720, Mn was 4,900, and Mw/Mn was 1.78. The results are shown in Table 3.

Example 18

The same procedures as those of Example 7 were performed except that ethylene (1-cyclopentadienyl)(fluorenyl) zirconium dichloride was changed to (1-cyclopentadienyl)(ocatamethyloctahydrodibenzofluorenyl)zirconium dichloride, 1-decene as a monomer was changed to 1-tetradecene, the polymerization temperature was changed to 50° C., and the amount of hydrogen was changed to 35 liter/hr.

The weight of the resulting transparent liquid polymer was 39.20 kg, and the polymerization activity was 19.60 kg-polymer/mmol-Zr/hr. The polymer was analyzed. [η] was 0.06 dl/g, Mw was 9,680, Mn was 6,150, and Mw/Mn was 1.57. The results are shown in Table 3.

TABLE 3

| | Component (A) | | Component | | | Temperature | Time | Monomer charging amount | | |
|---|---|---|---|---|---|---|---|---|---|---|
| | | | (B) | | | | | Ethylene | Hydrogen | 1-Decene |
| Example | Kind | mmol | Kind | mmol | Kind | mmol | (° C.) | (min) | (l/h) | (l/h) | (ml) |
| Example 7 | a | 0.002 | — | — | MAO | 2 | 90 | 60 | — | 20 | 250 |
| Example 8 | a | 0.002 | — | — | MAO | 2 | 60 | 60 | — | 10 | 250 |
| Example 9 | a | 0.002 | — | — | MAO | 2 | 90 | 60 | — | 50 | 250 |
| Example 10 | a | 0.002 | I | 0.04 | TIBA | 2 | 60 | 60 | — | 10 | 250 |
| Example 11 | a | 0.002 | — | — | MAO | 2 | 60 | 60 | 50 | 10 | 100 |
| Example 12 | a | 0.002 | — | — | MAO | 2 | 50 | 60 | — | 10 | — |

TABLE 3-continued

| | | | | | | | | | | | |
|---|---|---|---|---|---|---|---|---|---|---|---|
| Example 13 | a | 0.002 | — | — | MAO | 2 | 50 | 60 | — | 10 | — |
| Example 14 | a | 0.002 | — | — | MAO | 2 | 50 | 60 | — | 10 | — |
| Example 15 | d | 0.002 | — | — | MAO | 2 | 60 | 60 | — | 10 | 250 |
| Example 16 | a | 0.002 | — | — | MAO | 2 | 80 | 60 | — | 35 | 250 |
| Example 17 | a | 0.002 | — | — | MAO | 2 | 50 | 60 | — | 35 | — |
| Example 18 | a | 0.002 | — | — | MAO | 2 | 50 | 60 | — | 35 | — |

| | Monomer charging amount | | | | Polymerization | | | GPC | | |
|---|---|---|---|---|---|---|---|---|---|---|
| | 1-Octene | 1-Dodecene | 1-Tetradecene | Yield | activity | [η] | | | | |
| | (ml) | (ml) | (ml) | (g) | *1 | (dl/g) | | Mn | Mw | Mw/Mn |
| Example 7 | — | — | — | 97.17 | 48.59 | 0.04 | | 2,320 | 4,250 | 1.64 |
| Example 8 | — | — | — | 74.64 | 37.32 | 0.09 | | 7,220 | 13,360 | 1.85 |
| Example 9 | — | — | — | 77.34 | 38.67 | 0.06 | | 5,170 | 9,720 | 1.88 |
| Example 10 | — | — | — | 106.20 | 53.10 | 0.13 | | 13,700 | 22,670 | 1.65 |
| Example 11 | — | — | — | 49.49 | 24.74 | 0.16 | | 17,980 | 27,060 | 1.51 |
| Example 12 | 250 | — | — | 49.95 | 24.98 | 0.10 | | 9,380 | 16,700 | 1.63 |
| Example 13 | — | 250 | — | 29.59 | 14.80 | 0.10 | | 11,400 | 18,360 | 1.61 |
| Example 14 | — | — | 250 | 20.40 | 10.20 | 0.11 | | 14,460 | 23,570 | 1.63 |
| Example 15 | — | — | — | 28.25 | 14.13 | 0.08 | | 7,410 | 12,120 | 1.64 |
| Example 16 | — | — | — | 47.51 | 23.76 | 0.07 | | 5,860 | 9,910 | 1.69 |
| Example 17 | — | 250 | — | 45.30 | 22.65 | 0.07 | | 4,900 | 8,720 | 1.78 |
| Example 18 | — | — | 250 | 39.20 | 19.60 | 0.06 | | 6,150 | 9,680 | 1.57 | a: Ethylene(1-cyclopentadienyl)(fluorenyl)zirconium dichloride
d: Ethylene(1-cyclopentadienyl)(2,7-di-tert-butyl-fluorenyl)zirconium dichloride
e: Ethylene(1-cyclopentadienyl)(octamethyloctahydrodibenzofluorenyl)zirconium dichloride
I: N,N-dimethylanilinium tetrakis(pentafluorophenyl)borate
MAO: Methylaluminoxane
TIBA: Triisobutylaluminium
*1: kg-Polymer/mmol-Zr/hr

We claim:

1. A process for preparing a low molecular weight olefin (co)polymer having a molecular distribution (Mw/Mn) of 3 or smaller measured by gel permeation chromatography (GPC), comprising homopolymerizing or copolymerizing an olefin in which ethylene is used as a main monomer, and in a temperature range of 100° to 250° C., in the presence of an olefin polymerization catalyst comprising:
   (A) a Group 4 transition metal compound represented by the following formula (1), and
   (B) at least one compound selected from the group consisting of (B-1) an organometallic compound, (B-2) an organoaluminum compound, (B-3) an organoaluminum oxy-compound, and (B-4) a compound that reacts with the Group 4 transition metal compound (A) to form an ion pair;

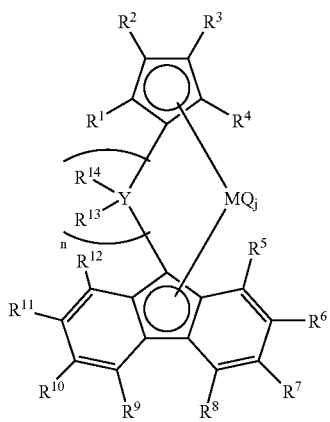

(1)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are independently selected from the group consisting of hydrogen, a hydrocarbon group, and a silicon-containing group, and are the same or different; and each adjacent pair of substituents $R^1$ to $R^{14}$ may be taken together to form a ring, M is Ti, Zr or Hf; Y is a Group 14 atom; each Q is independently selected from the group consisting of: a halogen, a hydrocarbon group, a neutral conjugated or non-conjugated diene having 10 or fewer carbon atoms, an anionic ligand, and a neutral ligand that can be coordinated with a lone electron pair; n is an integer of from 2 to 4; and j is an integer of from 1 to 4; wherein an intrinsic viscosity [η] of the low molecular weight olefin (co)polymer measured in decalin at 135° C. is 0.6 dl/g or less.

2. The process for preparing a low molecular weight olefin (co)polymer according to claim 1, wherein the intrinsic viscosity [η] of the low molecular weight olefin (co)polymer measured in decalin at 135° C. is 0.4 dl/g or less.

3. The process for preparing a low molecular weight olefin (co)polymer according to claim 1, wherein the low molecular weight olefin (co)polymer is obtained by homopolymerizing ethylene or copolymerizing ethylene which is a main monomer with one or more olefin(s) having 3 to 20 carbon atoms.

4. The process for preparing a low molecular weight olefin (co)polymer according to claim 1, wherein the Group 4 transition metal compound represented by the formula (1) is a Group 4 transition metal compound represented by the following formula (1');

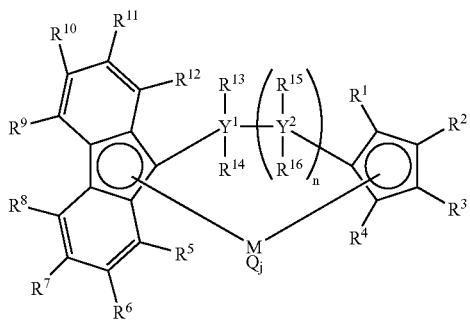

(1')

wherein $R^1$, $R^2$, $R^3$, $R^4$, $R^5$, $R^6$, $R^7$, $R^8$, $R^9$, $R^{10}$, $R^{11}$ and $R^{12}$ are independently selected from the group consisting of a hydrogen atom, a hydrocarbon group, and a silicon-containing group, and are the same or different; $R^{13}$, $R^{14}$, $R^{15}$ and $R^{16}$ are a hydrogen atom or a hydrocarbon group; n is an integer of from 1 to 3 and when n is 1, not all of the groups $R^1$ to $R^{16}$ are hydrogen atoms, and each of the groups $R^1$ to $R^{16}$ may be the same or different; each adjacent pairs of substituents $R^5$ to $R^{12}$ may be taken together to form a ring; $R^{13}$ and $R^{15}$ may be taken together to form a ring, or the pair of $R^{13}$ and $R^{15}$ and the pair of $R^{14}$ and $R^{16}$ may be taken together to form rings simultaneously; $Y^1$ and $Y^2$ are Group 14 atoms, and may be the same or different from each other, M is Ti, Zr or Hf; each Q is independently selected from the group consisting of a halogen, a hydrocarbon group, an anionic ligand and a neutral ligand that can be coordinated with a lone electron pair; and j is an integer of from 1 to 4.

5. The process for preparing a low molecular weight olefin (co)polymer according to claim 1, wherein an average residence time of the polymerization is 2 hours or less.

6. The process of claim 1, wherein the homopolymerizing or copolymerizing is conducted within a temperature range of 130° to 200° C.

7. The process of claim 3, wherein the homopolymerizing or copolymerizing is conducted within a temperature range of 130° to 200° C.

* * * * *